US012606608B2

(12) United States Patent
Hartwig et al.

(10) Patent No.: US 12,606,608 B2
(45) Date of Patent: Apr. 21, 2026

(54) MODIFIED NK-92 CELLS, AND THERAPEUTIC AND DIAGNOSTIC USES THEREOF

(71) Applicant: Universitätsmedizin der Johannes Gutenberg-Universität Mainz, Mainz (DE)

(72) Inventors: Udo Hartwig, Nackenheim (DE); Jan Wernersbach, Mainz (DE); Catherine Woelfel, Mainz (DE)

(73) Assignee: Universitatsmedizin Der Johannes Gutenberg-Univeristat Mainz, Mainz (DE)

( * ) Notice: Subject to any disclaimer, the term of this patent is extended or adjusted under 35 U.S.C. 154(b) by 1049 days.

(21) Appl. No.: 17/614,900

(22) PCT Filed: Jun. 9, 2020

(86) PCT No.: PCT/EP2020/065907
§ 371 (c)(1),
(2) Date: Nov. 29, 2021

(87) PCT Pub. No.: WO2020/249537
PCT Pub. Date: Dec. 17, 2020

(65) Prior Publication Data
US 2022/0233596 A1 Jul. 28, 2022

(30) Foreign Application Priority Data
Jun. 13, 2019 (EP) .................................... 19180008

(51) Int. Cl.
| | |
|---|---|
| C07K 14/73 | (2006.01) |
| A61K 40/11 | (2025.01) |
| A61K 40/15 | (2025.01) |
| A61K 40/32 | (2025.01) |
| A61K 40/42 | (2025.01) |
| A61P 35/02 | (2006.01) |
| C07K 14/705 | (2006.01) |
| C07K 14/725 | (2006.01) |
| C12N 5/0783 | (2010.01) |

(52) U.S. Cl.
CPC ........ *C07K 14/70514* (2013.01); *A61K 40/11* (2025.01); *A61K 40/15* (2025.01); *A61K 40/32* (2025.01); *A61K 40/4224* (2025.01); *A61P 35/02* (2018.01); *C07K 14/7051* (2013.01); *C07K 14/70517* (2013.01); *C12N 5/0646* (2013.01)

(58) Field of Classification Search
None
See application file for complete search history.

(56) References Cited

U.S. PATENT DOCUMENTS

2016/0083449 A1 3/2016 Schmitt et al.

FOREIGN PATENT DOCUMENTS

| WO | WO2016116601 | 7/2016 | |
|---|---|---|---|
| WO | WO-2016116601 A1 * | 7/2016 | ............. A61K 35/17 |
| WO | WO2018129199 | 7/2018 | |

OTHER PUBLICATIONS

Mahdavi et al., "production and characterization of new anti-her2 monoclonal antibodies" Monoclonal Antibodies in Immunodiagnosis and Immunotherapy (Year: 2015).*
Mensali et al. "NK cells specifically TCR dressed to kill cancer cells" Ebiomedicine (Year: 2019).*
Weng "Numbers and odds: TCR reportoire size and its age changes impacting on T cell functions" Semin Immunol (Year: 2023).*
Schaefer and Rost, "predict impact of single amino acid change upon protein structure" BMC Genomics (Year: 2012).*
Schaefer & Rost, "Impact impact of single amino acid change upon protein structure" BMC GEnomics (Year: 2012).*
Spinsanti, P. et al., "Wilms' tumor gene expression by normal and malignant human B lymphocytes", Leukemia & Lymphoma, vol. 38(5-6), pp. 611-619, Database Medline[Online], XP002795789, database aaccession No. NLM10953983, (Aug. 2000).
Wernersbach, J. et al., "PF439 exploring the therapeutic potential of t-cell-receptor redirected CD3+ natural killer cells for adoptive cellular therapy to acute myeloid leukemia", Hemasphere, vol. 3(S1), pp. 172-173, doi: 10.1097/01.HS9.0000559968.36666.57, XP55729111, (Jun. 2019).
Cheng, M. et al., "Natural killer cell lines in tumor immunoltherapy", Frontiers in Medicine., vol. 6(1), pp. 56-66, doi: 10.1007/s11684-012-0177-7, (Mar. 2012) Abs.
Sharpe, M. et al., "Genetically modified T cells in cancer therapy: opportunities and challenges", Dis. Model Mech., vol. 8(4), pp. 337-350, (Apr. 2015).
Mensali, N. et al., "NK cells specifically TCR-dressed to kill cancer cells", EBioMedicine, vol. 40, pp. 106-117, (2019).
Arai, S. et al., "Infusion of the allogeneic cell line NK-92 in patients with advanced renal cell cancer or melanoma: a phase I trial", Cytotherapy, vol. 10(6), pp. 625-632, (2008).
Tonn, T. et al., "Treatment of patients with advanced cancer with the natural killer cell line NK-92", Cytotherapy, vol. 15(12), pp. 1563-1570, (Dec. 2013).
Klingemann, H. et al., "Natural killer cells for immunotherapy—advantages of the NK-92 cell line over blookd NK cells", Frontiers in Immunology, vol. 7, pp. 1-7, (Mar. 2016).
Pinz, K. et al., "Targeting T-cell malignancies using anti-CD4 Car NK-92 cells", Oconotarget, vol. 8(68), pp. 112783-112796, (2017).
Zhao, Y. et al., "A herceptin-based chimeric antigen receptor with modified signaling domains leads to enhanced survival of transduced T lymphocytes and antitumor activity", Journal of Immunology, vol. 183(9), pp. 5563-5574, (Nov. 2009).

(Continued)

*Primary Examiner* — Robert M Kelly
*Assistant Examiner* — John David Moore
(74) *Attorney, Agent, or Firm* — McHale & Slavin, P.A.

(57) ABSTRACT
Modified natural killer 92 (NK-92) cells and their use in cancer therapy, in particular for the prevention or treatment of solid tumours such as sarcomas, carcinomas, melanoma and lymphoma, and non-solid tumours such as leukaemia and related disorders. Embodiments of the invention further relate to the use of the modified NK-92 cells for in vitro diagnosis, diagnostics and/or screening, methods for the preparation of a modified NK-92 that is specific for a target antigen of a target cell in a subject, and to an expression vector, comprising the nucleic acid sequences of an antigen-specific functional T cell receptor (TCR), CD3, CD4 and/or CD8.

13 Claims, 18 Drawing Sheets
Specification includes a Sequence Listing.

(56)                    References Cited

OTHER PUBLICATIONS

Enblad, G. et al., "Third generation CD19-CAR T cells for relapsed and refractory lymphoma and leukemia report from the Swedish Phase I/IIa trial", Blood, vol. 126(23), (Dec. 2015).

Tam, Y. et al., "Ex vivo expansion of the highly cytotoxic human natural killer-92 cell-line under current good manufacturing practice conditions for clinical adoptive cellular immunotherapy", Cytotherapy, vol. 5(3), pp. 259-272, doi: 10.1080/14653240310001523, (2003).

Tonn, T. et al., "Cellular immunotherapy of malignancies using the clonal natural killer line NK-92", Journal of Hematotherapy & Stem Cell Research, vol. 10(4), https://doi.org/10.1089/15258160152509145, (Jul. 2004).

Williams, B. et al., "A phase I trial of NK-92 cells for refractory hematological malignancies relapsing after autologous hematopoietic cell transplantation shows safety and evidence of efficacy", Oncotarget, vol. 8(51), pp. 89256-89268, 2017).

Zhang, J. et al., "Natural killer cells and current applications of chimeric antigen receptor-modified NK-92 cells in tumor immunotherapy", Intl. J. of Molecular Sciences, vol. 20(317), pp. 1-20, (2019).

Oelsner, S. et al., "Continuously expanding CAR NK-92 cells display selective cytotoxicity against B-cell leukemia and lymphoma", Cytotherapy, vol. 19(2), pp. 235-249, Online article: http://orca.cf.ac.uk/96745, (Apr. 2016).

Boublikova, L. et al., "Wilms tumor gene 1 (WT1), TP53, RAS/BRAF and KIT aberrations in testicular germ cell tumors", Cancer Letters, vol. 376(2), pp. 367-376, doi: https://doi.org/10.1016/j.canlet.2016.04.016, (Jul. 2016).

Gong, J. et al., "Characterization of a human cell line (NK-92) with phenotypical and functional characteristics of activated natural killer cells", Leukemia, vol. 8(4), pp. 652-658, (Apr. 1994).

Birkholz, K. et al., "A fast and robust method to clone and functionally validate T-cell receptors", J. Immunol. Methods, vol. 346(1-2), pp. 45-54, doi: 10.1016/j.jim.2009.05.001, (Jul. 2009).

Szymczak, A. et al., "Correction of multi-gene deficiency in vivo using a single 'self-cleaving' 2A peptide-based retroviral vector", Nat. Biotechnol., vol. 22(5), pp. 589-594, doi: 10.1038/nbt957, (May 2004).

* cited by examiner

Expression of activating and inhibiting receptors

SEQUENCE LISTING

```
<160> NUMBER OF SEQ ID NOS: 12

<210> SEQ ID NO 1
<211> LENGTH: 789
<212> TYPE: DNA
<213> ORGANISM: Artificial Sequence
<220> FEATURE:
<223> OTHER INFORMATION: TCR 5B2 alpha chain contains Homo sapiens and
      Mus musculus sequences

<400> SEQUENCE: 1
atgctgctgg aacatctgct gatcatcctg tggatgcagc tgacctgggt gtccggccag         60
cagctgaacc agagccccca gagcatgttc atccaggaag gcgaggacgt ctccatgaac        120
tgcaccagca gcagcatctt caacacctgg ctgtggtaca agcaggaccc cggcgagggc        180
cctgtgctgc tgatcgccct gtataaggcc ggcgagctga ccagcaacgg ccggctgaca        240
```

```
gcccagttcg gcattacccg gaaggacagc ttcctgaaca tcagcgccag catccccagc          300
gacgtgggca tctactttg cgccggcaac cagggcgccc agaaactggt gttcggccag           360
ggcacccggc tgaccatcaa cccccagaac cccgagcccg ccgtgtacca gctgaaggac          420
cccagaagcc aggacagcac cctgtgcctg ttcaccgact tcgacagcca gatcaacgtg          480
cccaagacca tggaaagcgg caccttcatc accgataagt gcgtgctgga catgaaggcc          540
atggacagca gagcaacggc cgccattgcc tggtccaacc agaccagctt cacatgccag          600
gacatcttca agagacaaac gccacctac cccagcagcg acgtgccctg tgacgccacc           660
ctgaccgaga gtccttcga dacagacatg aacctgaact tccagaacct gagcgtgatg           720
ggcctgagaa tcctgctgct gaaggtggcc ggcttcaacc tgctgatgac cctgcggctg          780
tggtccagc                                                                   789

<210> SEQ ID NO 2
<211> LENGTH: 927
<212> TYPE: DNA
<213> ORGANISM: Artificial Sequence
<220> FEATURE:
<223> OTHER INFORMATION: TCR 5B2 beta chain contains Homo sapiens and
      Mus musculus sequences

<400> SEQUENCE: 2
atgggcacca gactgctgtg ctgggccgct ctgtgtctgc tgggcgccga actgactgaa           60
gccggcgtgg cccagagccc cagatacaag atcatcgaga agcggcagag cgtggccttc          120
tggtgcaacc ccatcagcgg ccacgccaca ctgtactggt atcagcagat cctgggccag          180
ggccccaagc tgctgatcca gttccagaac aacggcgtgg tggacgacag ccagctgccc          240
aaggaccggt tcagcgccga gagactgaag ggcgtggact ccaccctgaa gatccagccc          300
gccaagctgg aagatagcgc cgtgtatctg tgcgccagca gcacctccgg cgccagcaac          360
acaggcgagc tgttcttcgg cgagggcagc agactgaccg tgctggaaga tctgagaaac          420 gtgaccccc ccaaggtgtc cctgttcgag cccagcaagg ccgagatcgc caacaagcag          480
aaagccaccc tggtctgcct ggccagaggc ttcttccccg accacgtgga actgtcttgg          540
tgggtgaacg gcaaagaggt gcacagcggc gtctgcaccg acccccaggc ctacaaagag          600
agcaactaca gctactgcct gagcagccgg ctgagagtgt ccgccacctt ctggcacaac          660
ccccggaacc acttcaggtg ccaggtgcag ttccacggcc tgagcgaaga ggacaagtgg          720
cccgagggca gccccaagcc cgtgacccag aatatctccg ccgaggcctg gggcagagcc          780
gactgtggca tcaccagcgc cagctaccac cagggcgtgc tgagcgccac catcctgtac          840
gagatcctgc tgggcaaggc caccctgtac gccgtgctgg tgtctggcct ggtgctgatg          900
gccatggtga aaagaaaaa cagctga                                                927

<210> SEQ ID NO 3
<211> LENGTH: 804
<212> TYPE: DNA
<213> ORGANISM: Artificial Sequence
<220> FEATURE:
<223> OTHER INFORMATION: TCR 25F2 alpha chain contains Homo sapiens and
      Mus musculus sequences

<400> SEQUENCE: 3
atgatgaagt ccctgcgggt gctgctggtg atcctgtggc tgcagctgag ctgggtgtgg           60
tcccagcaga aagaggtgga acaggaccct ggcccctga gcgtgccaga gggcgccatc          120
gtgtccctga actgcaccta cagcaacagc gccttccagt acttcatgtg gtacagacag          180
```

-continued

```
tacagccgga agggccccga gctgctgatg tacacctaca gctccggcaa caaagaggac     240
ggccggttca ccgcccaggt ggacaagagc agcaagtaca tcagcctgtt catccgggac     300
agccagccca gcgacagcgc cacctacctg tgcgccatga agtccagcgg cacctacaag     360
tacatcttcg gcaccggcac ccggctgaag gtgctggccc agaatcccga gccgccgtg     420 taccagctga aggaccccag aagccaggac agcaccctgt gcctgttcac cgacttcgac     480
agccagatca cgtgcccaa gaccatggaa agcggcacct tcatcaccga taagtgcgtg     540
ctggacatga aggccatgga cagcaagagc aacggcgcca ttgcctggtc caaccagacc     600
agcttcacat gccaggacat cttcaaagag acaaacgcca catccccag cagcgacgtg     660 ccctgcgacg ccaccctgac cgagaagtcc ttcgagacag acatgaacct gaacttccag     720
aacctgagcg tgatgggcct gcggatcctg ctgctgaagg tggccggctt caacctgctg     780
atgaccctgc ggctgtggtc cagc                                           804
```

<210> SEQ ID NO 4
<211> LENGTH: 921
<212> TYPE: DNA
<213> ORGANISM: Artificial Sequence
<220> FEATURE:
<223> OTHER INFORMATION: TCR 25F2 beta chain contains Homo sapiens and
      Mus musculus sequences

<400> SEQUENCE: 4

```
atggacagct ggaccttctg ctgcgtgtcc ctgtgcatcc tggtggccaa gcacaccgac      60
gccggcgtga tccagagccc cagacacgaa gtgaccgaga tgggccagga agtgaccctg     120
cgctgcaagc ccatcagcgg ccacaacagc ctgttctggt acaggcagac catgatgcgg     180
ggcctggaac tgctgatcta cttcaacaac aatgtgccca tcgacgacag cggcatgccc     240
gaggaccggt tcagcgccaa gatgcccaac gccagcttca gcaccctgaa gatccagccc     300
tccgagcccc gggacagcgc cgtgtacttt tgtgccagcg tgccaggcgg cagaaccggc     360
gagctgttct cggcgaggg cagcagactg accgtgctgg aggacctgag aaacgtgacc     420 cccccaagg tgtccctgtt cgagcccagc aaggccgaga tcgccaacaa gcagaaagcc     480
accctggtct gcctggccag aggcttcttc cccgaccacg tggaactgtc ttggtgggtg     540
aacggcaaag aggtgcacag cggcgtctgc accgaccccc aggcctacaa agagagcaac     600
tacagctact gcctgagcag ccggctgaga gtgtccgcca ccttctggca caaccccgg     660 aaccacttca ggtgccaggt gcagttccac ggcctgagcg aagaggacaa gtggcccgag     720
ggcagcccca gcccgtgac ccagaatatc agcgccgagg cctggggcag agccgactgt     780
ggcatcacca cgccagcta ccaccagggc gtgctgagcg ccaccatcct gtacgagatc     840
ctgctgggca aggccaccct gtacgccgtg ctggtgtccg gcctggtgct gatggccatg     900
gtgaaaaaga aaacagctg a                                              921
```

<210> SEQ ID NO 5
<211> LENGTH: 792
<212> TYPE: DNA
<213> ORGANISM: Artificial Sequence
<220> FEATURE:
<223> OTHER INFORMATION: TCR 5H11 alpha chain contains Homo sapiens and
      Mus musculus sequences

<400> SEQUENCE: 5

```
atgctgctgg aacatctgct gatcatcctg tggatgcagc tgacctgggt gtccggccag      60
```

-continued

```
cagctgaacc agagccccca gagcatgttc atccaggaag gcgaggacgt ctccatgaac      120
tgcaccagca gcagcatctt caacacctgg ctgtggtaca agcaggaccc cggcgagggc      180
cctgtgctgc tgatcgccct gtataaggcc ggcgagctga ccagcaacgg ccggctgaca      240
gcccagttcg gcattacccg gaaggacagc ttcctgaaca tcagcgccag catccccagc      300
gacgtgggca tctactttg cgccggcaac cagggcgccc agaaactggt gttcggccag       360
ggcacccggc tgaccatcaa cccccagaac cccgagcccg ccgtgtacca gctgaaggac      420
cccagaagcc aggacagcac cctgtgcctg ttcaccgact tcgacagcca gatcaacgtg      480
cccaagacca tggaaagcgg caccttcatc accgataagt gcgtgctgga catgaaggcc      540
atggacagca gagcaacgg cgccattgcc tggtccaacc agaccagctt cacatgccag       600
gacatcttca aagagacaaa cgccacctac cccagcagcg acgtgccctg tgacgccacc      660
ctgaccgaga agtccttcga gacagacatg aacctgaact tccagaacct gagcgtgatg      720
ggcctgagaa tcctgctgct gaaggtggcc ggcttcaacc tgctgatgac cctgcggctg      780
tggtccagct ga                                                         792
```

```
<210> SEQ ID NO 6
<211> LENGTH: 921
<212> TYPE: DNA
<213> ORGANISM: Artificial Sequence
<220> FEATURE:
<223> OTHER INFORMATION: TCR 5H11 beta chain contains Homo sapiens and
      Mus musculus sequences

<400> SEQUENCE: 6
atgggcagct ggaccctgtg ctgtgtgtcc ctgtgtattc tggtggccaa gcacaccgat      60
gccggcgtga tccagtctcc tagacacgaa gtgaccgaga tgggccaaga ggtcacactg      120
agatgcaagc ccatcagcgg ccacaacagc ctgttctggt acagacagac catgatgaga      180
ggcctggaac tgctgatcta cttcaacaac aacgtgccca tcgatgacag cggcatgccc      240
gaggatagat tcagcgccaa gatgcccaat gccagcttca gcaccctgaa gatccagcct      300
agcgagccta gagacagcgc cgtgtacttt tgtgcctctt ctctcggcgg cgtgggcaat      360
cagcctcagc actttggaga tggcacccgg ctgagcatcc tggaagatct gagaaacgtg      420
acccctccta agtgtctct gttcgagccc tctaaggccg agatcgccaa caagcagaaa       480
gccacacttg tgtgcctggc cagaggcttc ttccccgatc atgtggaact gtcttggtgg      540
gtcaacggca agaggtgca cagcggagtc tgtaccgatc ctcaggccta caaagagagc        600
aactacagct actgcctgag cagcagactg agagtgtccg ccaccttctg gcacaacccc      660
agaaaccact tcagatgcca ggtgcagttt cacggcctga gcgaagagga taagtggcct      720
gagggaagcc ccaagcctgt gacacagaat atttctgccg aagcctgggg cagagccgat      780
tgtggaatca catctgccag ctaccaccag ggcgtgctga gcgccacaat cctgtatgag      840
atcctgctgg gcaaagccac tctgtacgca gtgctggtgt ctggactggt gctgatggcc      900
atggtcaaga gaagaatag c                                                921
```

```
<210> SEQ ID NO 7
<211> LENGTH: 711
<212> TYPE: DNA
<213> ORGANISM: Homo sapiens

<400> SEQUENCE: 7
gccaccatgg ccttaccagt gaccgccttg ctcctgccgc tggccttgct gctccacgcc      60
```

```
gccaggccga gccagttccg ggtgtcgccg ctggatcgga cctggaacct gggcgagaca     120
gtggagctga agtgccaggt gctgctgtcc aacccgacgt cgggctgctc gtggctcttc     180
cagccgcgcg gcgccgccgc cagtcccacc ttcctcctat acctctccca aaacaagccc     240
aaggcggccg aggggctgga cacccagcgg ttctcgggca agaggttggg ggacaccttc     300
gtcctcaccc tgagcgactt ccgccgagag aacgagggct actatttctg ctcggccctg     360
agcaactcca tcatgtactt cagccacttc gtgccggtct tcctgccagc gaagcccacc     420
acgacgccag cgccgcgacc accaacaccg gcgcccacca tcgcgtcgca gcccctgtcc     480
ctgcgcccag aggcgtgccg gccagcggcg gggggcgcag tgcacacgag ggggctggac     540
ttcgcctgtg atatctacat ctgggcgccc ctggccggga cttgtggggt ccttctcctg     600
tcactggtta tcacccttta ctgcaaccac aggaaccgaa gacgtgtttg caaatgtccc     660
cggcctgtgg tcaaatcggg gagacaagcc agcctttcgg cgagatacgt c             711
```

```
<210> SEQ ID NO 8
<211> LENGTH: 600
<212> TYPE: DNA
<213> ORGANISM: Homo sapiens

<400> SEQUENCE: 8
gccaccatgg ccttaccagt gaccgccttg ctcctgccgc tggccttgct gctccacgcc      60
gccaggccga gccagttccg ggtgtcgccg ctggatcgga cctggaacct gggcgagaca     120
gtggagctga agtgccaggt gctgctgtcc aacccgacgt cgggctgctc gtggctcttc     180
cagccgcgcg gcgccgccgc cagtcccacc ttcctcctat acctctccca aaacaagccc     240
aaggcggccg aggggctgga cacccagcgg ttctcgggca agaggttggg ggacaccttc     300
gtcctcaccc tgagcgactt ccgccgagag aacgagggct actatttctg ctcggccctg     360
agcaactcca tcatgtactt cagccacttc gtgccggtct tcctgccagc gaagcccacc     420
acgacgccag cgccgcgacc accaacaccg gcgcccacca tcgcgtcgca gcccctgtcc     480
ctgcgcccag aggcgtgccg gccagcggcg gggggcgcag ggaaccgaag acgtgtttgc     540
aaatgtcccc ggcctgtggt caaatcggga gacaagccca gcctttcggc gagatacgtc     600
```

```
<210> SEQ ID NO 9
<211> LENGTH: 669
<212> TYPE: DNA
<213> ORGANISM: Homo sapiens

<400> SEQUENCE: 9
ctccagcaga cccctgcata cataaaggtg caaaccaaca agatggtgat gctgtcctgc      60
gaggctaaaa tctccctcag taacatgcgc atctactggc tgagacagcg ccaggcaccg     120
agcagtgaca gtcaccacga gttcctggcc ctctgggatt ccgcaaaagg gactatccac     180
ggtgaagagg tggaacagga gaagatagct gtgtttcggg atgcaagccg gttcattctc     240
aatctcacaa gcgtgaagcc ggaagacagt ggcatctact tctgcatgat cgtcgggagc     300
cccgagctga ccttcgggaa gggaactcag ctgagtgtgg ttgatttcct tcccaccact     360
gcccagccca ccaagaagtc caccctcaag aagagagtgt gccggttacc caggccagag     420
acccagaagg gcccactttg tagccccatc acccttggcc tgctggtggc tggcatcctg     480
gttctgctgg tttccctggg agtggccatc cacctgtgct gccggcggag gagagcccgg     540
cttcgtttca tgaaacagcc tcaagggggaa ggtgtatcag gaacctttgt cccccaatgc     600
ctgcatggat actacagcaa tactacaacc tcacagaagc tgcttaaccc atggatcctg     660
```

-continued

```
aaaacatag                                                              669

<210> SEQ ID NO 10
<211> LENGTH: 603
<212> TYPE: DNA
<213> ORGANISM: Homo sapiens

<400> SEQUENCE: 10
ctccagcaga cccctgcata cataaaggtg caaaccaaca agatggtgat gctgtcctgc        60
gaggctaaaa tctccctcag taacatgcgc atctactggc tgagacagcg ccaggcaccg       120
agcagtgaca gtcaccacga gttcctggcc ctctgggatt ccgcaaaagg gactatccac       180
ggtgaagagg tggaacagga gaagatagct gtgtttcggg atgcaagccg gttcattctc       240
aatctcacaa gcgtgaagcc ggaagacagt ggcatctact tctgcatgat cgtcgggagc       300
cccgagctga ccttcgggaa gggaactcag ctgagtgtgg ttgatttcct tcccaccact       360
gcccagccca ccaagaagtc caccctcaag aagagagtgt gccggttacc caggccagag       420
acccagaagg gcccactttg tagccccatc acccttggcc tgctggtggc tggcgtcctg       480
gttctgctgg tttccctggg agtggccatc cacctgtgct gccggcggag gagagcccgg       540
cttcgtttca tgaaacaact aagattacat ccactggaga aatgttccag aatggactac       600
tga                                                                    603

<210> SEQ ID NO 11
<211> LENGTH: 570
<212> TYPE: DNA
<213> ORGANISM: Homo sapiens

<400> SEQUENCE: 11
ctccagcaga cccctgcata cataaaggtg caaaccaaca agatggtgat gctgtcctgc        60
gaggctaaaa tctccctcag taacatgcgc atctactggc tgagacagcg ccaggcaccg       120
agcagtgaca gtcaccacga gttcctggcc ctctgggatt ccgcaaaagg gactatccac       180
ggtgaagagg tggaacagga gaagatagct gtgtttcggg atgcaagccg gttcattctc       240
aatctcacaa gcgtgaagcc ggaagacagt ggcatctact tctgcatgat cgtcgggagc       300
cccgagctga ccttcgggaa gggaactcag ctgagtgtgg ttgatttcct tcccaccact       360
gcccagccca ccaagaagtc caccctcaag aagagagtgt gccggttacc caggccagag       420
acccagaagg gcccactttg tagccccatc acccttggcc tgctggtggc tggcgtcctg       480
gttctgctgg tttccctggg agtggccatc cacctgtgct gccggcggag gagagcccgg       540
cttcgtttca tgaaacaatt ttacaaatga                                       570

<210> SEQ ID NO 12
<211> LENGTH: 2373
<212> TYPE: DNA
<213> ORGANISM: Homo sapiens

<400> SEQUENCE: 12
atggaacata gcacgtttct ctctggcctg gtactggcta cccttctctc gcaagtgagc        60
cccttcaaga tacctataga ggaacttgag gacagagtgt tgtgaattg caataccagc       120 atcacatggg tagagggaac ggtgggaaca ctgctctcag acattacaag actggacctg       180 ggaaacgca tcctggaccc acgaggaata tataggtgta atgggacaga tatatacaag       240
gacaaagaat ctaccgtgca agttcattat cgaatgtgcc agagctgtgt ggagctggat       300
```

-continued

```
ccagccaccg tggctggcat cattgtcact gatgtcattg ccactctgct ccttgctttg     360
ggagtcttct gctttgctgg acatgagact ggaaggctgt ctggggctgc cgacacacaa     420
gctctgttga ggaatgacca ggtctatcag cccctccgag atcgagatga tgctcagtac     480
agccaccttg gaggaaactg ggctcggaac aagggaccgg tgaaacagac tttgaatttt     540
gaccttctca agttggcggg agacgtggag tccaacccag ggcccatgga acaggggaag     600
ggcctggctg tcctcatcct ggctatcatt cttcttcaag gtactttggc ccagtcaatc     660
aaaggaaacc acttggttaa ggtgtatgac tatcaagaag atggttcggt acttctgact     720
tgtgatgcag aagccaaaaa tatcacatgg tttaaagatg ggaagatgat cggcttccta     780
actgaagata aaaaaaaatg gaatctggga agtaatgcca aggaccctcg agggatgtat     840
cagtgtaaag gatcacagaa caagtcaaaa ccactccaag tgtattacag aatgtgtcag     900
aactgcattg aactaaatgc agccaccata tctggctttc tctttgctga aatcgtcagc     960
attttcgtcc ttgctgttgg ggtctacttc attgctggac aggatggagt tcgccagtcg    1020
agagcttcag acaagcagac tctgttgccc aatgaccagc tctaccagcc cctcaaggat    1080
cgagaagatg accagtacag ccaccttcaa ggaaaccagt tgaggaggaa tagaagatct    1140
gagggcagag gaagtctgct aacatgcggt gacgtcgagg agaatcctgg cccaatgcag    1200
tcgggcactc actggagagt tctgggcctc tgcctcttat cagttggcgt ttgggggcaa    1260
gatggtaatg aagaaatggg tggtattaca cagacaccat ataaagtctc catctctgga    1320
accacagtaa tattgacatg ccctcagtat cctggatctg aaatactatg gcaacacaat    1380
gataaaaaca taggcggtga tgaggatgat aaaaacatag gcagtgatga ggatcacctg    1440
tcactgaagg aattttcaga attggagcaa agtggttatt atgtctgcta ccccagagga    1500
agcaaaccag aagatgcgaa cttttatctc tacctgaggg caagagtgtg tgagaactgc    1560
atggagatgg atgtgatgtc ggtggccaca attgtcatag tggacatctg catcactggg    1620
ggcttgctgc tgctggttta ctactggagc aagaatagaa aggccaaggc caagcctgtg    1680
acacgaggag cgggtgctgg cggcaggcaa aggggacaaa acaaggagag gccaccacct    1740
gttcccaacc cagactatga gcccatccgg aaaggccagc gggacctgta ttctggcctg    1800
aatcagagac gcatcggagg atccgccacg aacttctctc tgttaaagca agcaggagac    1860
gtggaagaaa accccggtcc catgaagtgg aaggcgcttt tcaccgcggc catcctgcag    1920
gcacagttgc cgattacaga ggcacagagc tttggcctgc tggatcccaa actctgctac    1980
ctgctggatg gaatcctctt catctatggt gtcattctca ctgccttgtt cctgagagtg    2040
aagttcagca ggagcgcaga cgcccccgcg taccagcagg gccagaacca gctctataac    2100
gagctcaatc taggacgaag agaggagtac gatgttttgg acaagagacg tggccgggac    2160
cctgagatgg ggggaaagcc gagaaggaag aaccctcagg aaggcctgta caatgaactg    2220
cagaaagata agatggcgga ggcctacagt gagattggga tgaaaggcga gcgccggagg    2280
ggcaaggggc acgatggcct ttaccagggt ctcagtacag ccaccaagga cacctacgac    2340
gcccttcaca tgcaggccct gccccctcgc taa                                 2373
```

MODIFIED NK-92 CELLS, AND THERAPEUTIC AND DIAGNOSTIC USES THEREOF

CROSS REFERENCE TO RELATED APPLICATIONS

This is a national stage filing in accordance with 35 U.S.C. $371 of PCT/EP2020/065907, filed Jun. 9, 2020, which claims the benefit of the priority of European Patent Application No. 19180008.5, filed Jun. 13, 2019, the contents of each are incorporated herein by reference.

TECHNICAL FIELD

The present invention relates to modified natural killer 92 (NK-92) cells and their use in cancer therapy, in particular for the prevention or treatment of leukaemia and related disorders. The invention further relates to the use of the modified NK-92 cells for in vitro diagnosis, diagnostics and/or screening. Finally, the invention also relates to methods for the preparation of a modified NK-92 cell that is specific for a target antigen of a target cell in a subject. The invention also relates to an expression vector, comprising the nucleic acid sequences of an antigen-specific functional T cell receptor (TCR), CD3, CD4 and/or CD8.

BACKGROUND ART

Natural killer (NK) cells have the ability to recognize and kill tumour cells without the requirement of prior antigen exposure. In the recent years, NK cells have grown as promising agents for cell-based cancer immunotherapies. For example, NK cells have been used for T cell receptor (TCR) gene therapy by re-programming the cells to be specific for target antigens, such as tumour or viral antigens in complex with the major histocompatibility complex (MHC).

Accordingly, a TCR-mediated gene therapy is desired to redirect cytotoxic T cells towards selected epitopes of tumour antigens. The introduction of a functional TCR complex into NK cells that inherently detect and eliminate virally infected cells and/or tumour cells enhances the efficiency of identification and killing of these cells, and also circumvents the potential risk of TCR mispairing, i.e. to minimize the formation of mixed TCR dimers. TCR mispairing can significantly decrease the functional avidity of the genetically modified T cells by reducing the ability of the cells to interact with the desired target peptide and it thus potentially represents a risk for autoimmunity (Sharpe M et al., Genetically modified T cells in cancer therapy: opportunities and challenges. Dis Model Mech. 2015 April; 8(4): 337-350). TCR mispairing also has the potential to induce harmful recognition of self-antigens, resulting in graft versus host disease.

Several malignant NK cell lines, including NK-92, YT, NKL, HANK-1, KHYG-1, NK-YS and NKG have been described (Cheng M, Zhang J, Jiang W, Chen Y, Tian Z. Natural killer cell lines in tumour immunotherapy. Front Med 2012; 6: 56-66). Among these, NK-92 cells have been demonstrated to be a safe and potentially beneficial therapy with successful anti-tumour effects, receiving FDA approval for testing in patients with advanced malignant melanoma and renal cell carcinoma. NK-92 is currently the only NK cell line that has entered clinical trials and can serve as a platform for studying NK cell-based tumour immunotherapy in the future (Ljunggren H G, Malmberg K J. Prospects for the use of NK cells in immunotherapy of human cancer. Nat Rev Immunol 2007; 7: 329-339).

NK-92 can be turned into a T-cell-like effector cell by introducing the genes encoding the CD3 subunits (Mensali et al., NK cells specifically TCR-dressed to kill cancer cells; EBioMedicine (2019) 106-117). In contrast to T cells, TCR-NK-92 cells do not express any endogenous TCR. Moreover, recent clinical trials using NK-92 have shown that despite their allogeneic origin the NK-92 did not cause severe toxicities and were poorly immunogenic, and therefore not rejected by the host (Arai S, et al., Infusion of the allogeneic cell line NK-92 in patients with advanced renal cell cancer or melanoma: a phase 1 trial. Cytotherapy 2008; 10:625-32; Tonn T, et al., Treatment of patients with advanced cancer with the natural killer cell line NK-92. Cytotherapy 2013; 15:1563-70). NK-92 is also the only cell line product that has been infused into patients with advanced cancer with clinical benefit and minimal side effects (Hans Klingemann et al., Natural Killer Cells for Immunotherapy Advantages of the NK-92 Cell Line over Blood NK Cells, published in Frontiers in Immunology, March 2016, Volume 7).

A number of modified NK-92 cells have been prepared for use in cancer therapy and cell therapy. NK-92 cells were engineered to express a third generation CD4-specific CAR (CD4CAR) containing CD28,4-1 BB and CD3 signalling domains (Pinz K G et al., Targeting T-cell malignancies using anti-CD4 CAR NK-92 cells, Oncotarget, 2017; 8:112783-112796). Third generation CAR constructs have been associated with enhanced antitumour activity (Zhao Y et al., A Herceptin-based chimeric antigen receptor with modified signalling domains leads to enhanced survival of transduced T lymphocytes and antitumour activity. J Immunol Baltim Md 1950.2009; 183:5563-74; Enblad G. et al., Third Generation CD19-CAR T Cells for Relapsed and Refractory Lymphoma and Leukemia Report from the Swedish Phase I/IIa Trial. Blood. 2015; 126:1534-1534). CD4CAR NK-92 cells exhibit robust anti-tumour cytotoxicity ex vivo against both adult and pediatric CD4+ lymphoma/leukaemia cell lines, CD4+ T-cells isolated from umbilical cord blood, as well as against untreatable primary CD4+ T-cell malignancies from adult and pediatric patients.

In combination with current good manufacturing practice (cGMP)-compliant expansion methodologies, NK-92 cells are approved for analysis in clinical trials to determine their utility in the treatment of some types of malignant tumours (Tam, Y. K et al., Ex vivo expansion of the highly cytotoxic human natural killer-92 cell-line under current good manufacturing practice conditions for clinical adoptive cellular immunotherapy. Cytotherapy 2003, 5, 259-272; Tonn, T et al., Cellular immunotherapy of malignancies using the clonal natural killer cell line NK-92. J. Hematother. Stem Cell. Res. 2001, 10, 535-544; Klingemann, H. et al., Natural Killer Cells for Immunotherapy—Advantages of the NK-92 Cell Line over Blood NK Cells. Front. Immunol. 2016, 7, 91). For example, ex vivo expansion of NK-92 under current good manufacturing practice conditions for clinical adoptive cellular immunotherapy demonstrated that when NK-92 cells were irradiated with 500 cGy gamma rays, the proliferation of NK-92 cells was prevented, while their high killing activity was maintained. It has also been shown that irradiated NK-92 cells can be administered at very high doses with minimal toxicity in patients with refractory blood cancers, who had relapsed after autologous hematopoietic cell transplantation (AHCT). Therefore, high dose NK-92 therapy is considered to be safe and toxicity was minimal in the patients treated (Williams et al., A phase I trial of NK-92 cells for refractory haematological malignancies relapsing after autologous hematopoietic cell transplantation shows safety and evidence of efficacy, Oncotarget, 2017, Vol. 8, pp: 89256-89268).

In a different approach, the cytotoxic effects of CAR-CD19-CD3ζ-NK-92, CAR-CD19-CD28-CD3ζ-NK-92, and CAR-CD19-CD137-CD3ζ-NK-92 on established B-cell leukaemia and lymphoma cells have been compared, and the results showed that all three CD19-specific CAR-NK-92 cell lines were effective at killing B cell malignancies (Zhang et al., Natural Killer Cells and Current Applications of Chimeric Antigen Receptor-Modified NK-92 Cells in Tumor Immunotherapy, International Journal of Molecular Sciences, Publ. 14 Jan. 2019). However, CAR-CD19-CD137-CD3ζ-NK-92 cells were less effective than CAR-CD19-CD3ζ-NK-92 and CAR-CD19-CD28-CD3ζ-NK-92 cells at cell killing and cytokine production, indicating the differential effects of the costimulatory CD28 and CD137 domains. (Oelsner, S et al., Continuously expanding CAR NK-92 cells display selective cytotoxicity against B-cell leukaemia and lymphoma. Cytotherapy 2017, 19, 235-249).

WO 2018/129199 A1 relates to NK cells that express an antigen-specific functional T cell receptor (TCR) complex, wherein the antigen is preferably a tumour antigen or a tumour-associated antigen. The embodiment primarily focuses on the use of T cell receptor (TCR) genes for the genetic modification and retargeting of natural killer (NK) cells towards tumour-associated antigens (TAA), in an effort to develop a new approach in TCR gene therapy that circumvents the problems associated with mispairing of TCR chains.

WO 2016/116601 A1 describes natural killer cells and their use in therapy by expressing CD3 along with TCR to generate a NK-CD3-TCR cell line. It has been shown that NK-92-CD3 cells can be stimulated by CD4$^+$ T cell-derived TCRs. The described NK cell line shall not depend on CD4 and/or CD8 expression and the tested cell line is therefore CD4/CD8 co-receptor independent.

US 2016/083449 A1 relates to TCRs with high or enhanced affinity against a human Wilms tumor protein 1 (WT-1) epitope, T cells expressing such WT-1-specific TCRs, nucleic acids encoding the same, and compositions for use in treating diseases or disorders in which cells overexpress WT-1, such as in cancer. WT1 has been identified as a novel factor involved in TGCT pathogenesis, with a potential prognostic impact. Distinct biologic nature of the two types of relapses occurring in TGCT and differential mutation rate of the key TGCT-related genes have been documented (Boublikova L et al., Wilms tumor gene 1 (WT1), TP53, RAS/BRAF and KIT aberrations in testicular germ cell tumors, Cancer Lett. 2016 Jul. 1; 376(2):367-76. doi: 10.1016/j.canlet.2016.04.016. Epub 2016 Apr. 13; US National Library of Medicine (NLM), August 2000, Spinsanti P. et al. "Wilms' tumor gene expression by normal and malignant human B lymphocytes", Database accession no. NLM10953983).

Beside all these efforts, it remains a challenge to modify NK cells to be suitable for TCR gene therapy.

DISCLOSURE OF INVENTION

Against this background, it is object of the present invention to provide an alternative modified NK-92 cell, which is suitable for therapeutic and diagnostic applications, allowing the expression of different acute myeloid leukaemia (AML)-reactive TCRs to induce anti-leukemic immunity in vitro and in vivo.

This object is solved by a modified NK-92 cell expressing an antigen-specific T cell receptor TCR), CD3 and CD4 and/or CD8 to generate a NK-92-TCR-CD3$^+$-CD4$^+$ cell or NK-92-TCR-CD3$^+$-CD8$^+$ cell or NK-92-TCR-CD3$^+$-CD4$^+$-CD8$^+$ cell. The expression as used herein "TCR, CD3, CD4 and/or CD8" in the context of NK-92 refers to an NK-92 cell that expresses TCR, CD3, CD4 or TCR, CD3, CD8 or TCR, CD3, CD4, CD8, either as separate proteins or as part of a fusion protein. The term "modified NK-92" cell refers to a NK-92-TCR-CD3$^+$-CD4$^+$ cell or NK-92-TCR-CD3$^+$-CD8$^+$ cell or NK-92-TCR-CD3$^+$-CD4$^+$-CD8$^+$ cell.

The present invention is based on the recent developments of adoptive cellular therapy (ACT) with redirected T cells expressing a chimeric antigen receptor (CAR) or transgenic T-cell-receptor (tTCR). The technology has revolutionized cellular immunotherapy to haematological neoplasia, in particular to acute lymphoid leukaemia, and also appears to be suitable for the prevention or treatment for solid tumours. While CARs can only detect fully cell surface expressed target structures, TCR-mediated recognition is not limited to surface antigens, but covers processed tumour neoantigens derived from whole proteomes. However, mispairing of transgenic and endogenous TCRs and restriction to patient-derived, autologous T lymphocytes with variable "fitness" and T cell subsets due to individual health conditions and age of the patient exemplify the current limitations encountered in TCR-redirected ACT. One advantage is that the NK-92 elicits lytic activity comparable to T cells. In the context of therapeutic or diagnostic applications, the NK-92 cell line has been approved by the FDA for ACT and shown not to cause graft-vs-host disease (GvHD).

Although modified NK-92 cells expressing TCR and CD3 are described in the art, the present invention uses an alternative approach to provide a therapeutically-effective agent for targeting and killing cancer cells based on the FDA-approved NK-92 cell line. The modified NK-92 cell of the present invention is modified to express an antigen-specific TCR in order to kill target cells in a specific and directed way similar to T cells. Although co-expression of TCR and CD3 in NK cells was found to be sufficient for the TCR to localize to the surface of NK cells, the antigen specificity and cytotoxicity towards target cells can be further improved by co-expressing TCR-CD3 with CD4 and/or CD8 in genetically modified NK-92 cells which enables redirection of CD3 positive NK-92 cells with co-receptor dependent TCRs thereby extending their possible immuno-therapeutic application. Additionally, the co-expression of TCR-CD3-CD4/CD8 is mediated in a non-immunogenic NK-92 cell. This can be achieved, for instance, by irradiating NK-92 cells to prevent their proliferation such that the cells do not persist in a subject to be treated such that the cells could raise an immune response.

In a preferred embodiment of the present invention, a TCR is expressed which is specific for an antigen on a target cell, preferably a HLA-restricted peptide antigen derived from the transcriptome of the tumour cell. Preferably, the TCR expressed by the modified NK-92 cells of the present invention is specific for an antigen of a tumour cell. This means that the NK-92-TCR-CD3$^+$-CD4$^+$ cells or NK-92-TCR-CD3$^+$-CD8$^+$ cells or NK-92-TCR-CD3$^+$-CD4$^+$-CD8$^+$ cells of the invention can be used for cancer-specific therapy, wherein the NK-92 cells are non-immunogenic in the subject to be treated. This is achieved by a specific expression of TCR, CD3 and CD4/CD8 in the genetically engineered NK-92 cell of the invention. In an alternative embodiment, any other NK cell could be used to express TCR, CD3 and CD4/CD8, i.e. the scope of the invention may not be limited to NK-92 but may apply to any NK-cell known in the art.

Because the function of a given TCR in the modified NK-92 cells is CD4- and/or CD8-dependent, it is desirable to generate NK-92-TCR-CD3$^+$-CD4$^+$ cells or NK-92-TCR-CD3$^+$-CD8$^+$ cells or NK-92-TCR-CD3$^+$-CD4$^+$-CD8$^+$ cells that express a specific TCR for the prevention or treatment of a primary leukaemia or to diagnose the presence of tumour cells. Using the NK 92 cell line of the invention, both leukemic tumours and solid tumours can be targeted and treated by the cytolytic activity of the modified NK-92 cells.

In a further aspect of the present invention, the TCR expressed by the modified NK-92 cell of the invention has the ability of specifically binding to an antigen MHC complex on the surface of a target cell. Preferably, the target cell is a cancer cell or a virally infected cell.

The CD8 expressed on the surface of the modified NK-92 of the invention may by any CD8 that binds to MHC and comprises any α and β isoform as well as variants or derivatives thereof. The most common form of CD8 is composed of a CD8-α and CD8-β chain, whereas two variants for the α and several for the β chain exist.

The nucleic acid sequences for the antigen-specific TCR, CD8 and CD3 were cloned into an expression vector that has the ability to express TCR-CD3-CD4 and/or CD8 in NK-92 cells. Examples of such expression vectors are the plasmids shown in FIGS. 1 to 7 corresponding to pMXs_IRES_Puro TCR 25F2, pMXs_IRES_Puro TCR 5B2, pMXs_IRES_Puro TCR 5H11, pMXs_IRES_Neo_CD8α1β2, pMXs_IRES_Neo_CD8α1β5, pMXs_IRES_Neo_CD8α2β3, and pMXs_DEST_CD3-complex.

In a preferred embodiment of the present invention, the TCR originates from 5B2, 25F2 or 5H11 cells and thus the modified NK-92 cell carries the 5B2, 25F2 or 5H11-specific TCR domains.

In a first aspect of the present invention, the 5B2 TCR is composed of an alpha chain encoded by a nucleic acid sequence as defined in SEQ ID NO: 1 and a beta chain encoded by a nucleic acid sequence as defined in SEQ ID NO: 2, or degenerate variants thereof.

In a second aspect of the present invention, the 25F2 TCR is composed of an alpha chain encoded by a nucleic acid sequence as defined in SEQ ID NO: 3 and a beta chain encoded by a nucleic acid sequence as defined in SEQ ID NO: 4, or degenerate variants thereof.

In a third aspect of the present invention, the 5H11 TCR is composed of an alpha chain encoded by a nucleic acid sequence as defined in SEQ ID NO: 5 and a beta chain encoded by a nucleic acid sequence as defined in SEQ ID NO: 6, or degenerate variants thereof.

Preferred α- and β-chain of the TCRs 5H11, 25F2 and 5B2 are originally isolated from AML-reactive CTL clones. Preferred HLA alleles depicting the restriction element(s) utilized by each individual TCR comprising the α- and β-chain are TCR 5H11 (HLA-B*57:01 or HLA-CW*06:02), TCR 25F2 (HLA-B*58) and TCR 5B2 (HLA-CW*07:01). The constant parts of the α- and β-chains of the TCRs are formed by nucleotide sequences derived from *Mus musculus*, whereas the other domains are derived from *Homo sapiens*.

In a further embodiment, the TCRs described herein are co-expressed with any CD3 and CD4 and/or CD8 construct. Preferred CD8 constructs comprise CD8α and CD8β chains derived from cDNA isolated from AML-reactive CD8$^+$ CTL clones. Examples are the CD8α1 according to the nucleic acid sequence of SEQ ID NO: 7 or CD8α2 according to the nucleic acid sequence of SEQ ID NO: 8, CD8β2 according to the nucleic acid sequence of SEQ ID NO: 9, CD8β3 according to the nucleic acid sequence of SEQ ID NO: 10 or CD8β5 according to the nucleic acid sequence of SEQ ID NO: 11. An example of a CD3 construct is encoded by the nucleic acid sequence according to SEQ ID NO: 12.

The invention is not limited to the exact nucleic acid sequences shown in any of SEQ ID NO: 1 to 12 but also includes elongated, truncated or substituted forms of these sequences. It will be apparent for the person skilled in the art that the depicted nucleic acids are only examples and that the invention also includes variants both in modified and non-modified forms, including artificial and chemically modified nucleic acid bases. The invention also covers nucleic acid sequences that are degenerate variants of the sequences disclosed herein but code for the identical or similar amino acid in the resulting gene product.

The CD3, CD4 and/or CD8 complexes can be expressed individually or as part of a fusion protein together or along with TCR in the NK-92 cell. An example is a NK-92 cell expressing an antigen-specific TCR as a fusion protein together with CD3 in conjunction with CD8 and/or CD4.

The present invention comprises any NK-92 cell (Gong J H et al., Leukemia. 1994 April; 8(4):652-8.) or a variant thereof, or a modified form thereof, including but not limited to any immunogenic or non-immunogenic variants. The term "non-immunogenic" refers to the immunogenic property of the NK-92 cell of the invention and means that there is little or no contradictive immune response that could affect the function or biological effect of the cells. That said, the cells retain their cytotoxic activity in the subject to be treated, in particular their cytotoxic activity against a target cell.

The modified NK-92 cell of the present invention can be used as a medicament, i.e. as a non-immunogenic component of a pharmaceutical composition. A preferred target cell of the invention is a cancer cell and therefore the modified NK-92 cell of the invention is suitable for cancer therapy.

As such it covers all solid and non-solid tumours that allow an application of TCR-expressing NK92 cells. Examples of solid tumours are different forms of sarcomas, carcinomas, melanoma and lymphoma.

The invention can be used for the prevention or treatment of both solid and haematopoietic cancers. A preferred cancer is leukaemia and related disorders, in particular acute myeloid leukaemia (AML), chronic lymphocytic leukaemia (CLL), acute lymphocytic leukaemia (ALL), chronic myeloid leukaemia (CML), chronic myelomonocytic leukaemia (CMML), eosinophilic leukaemia, hairy cell leukaemia, Hodgkin's lymphoma, multiple myeloma (MM), non-Hodgkin's lymphoma (NHL), myeloproliferative disorders or myelodysplastic syndrome. Further examples include the treatment of solid tumours such as acute myeloblastic leukaemia, acute monoblastic leukaemia, acute erythroleukemic leukaemia, acute megakaryosblastic leukaemia, acute myelomonocytic leukaemia or acute undifferentiated leukaemia.

Prior to administration to a patient, the modified NK-92 cells of the present invention are made non-immunogenic, preferably by irradiation, such that their time of survival is only limited in order to reduce severe side effects to the patient. In one embodiment of the present invention, the NK-92 cells may be administered to the subject intravenously. However, also an injection of the cells directly into tumour tissue (intratumoural), or an intraperitoneal administration is possible. The dose of administration will vary and depends on the patient's size, weight and condition. For example, $10^5$ to $10^{12}$ cells can be administered to a patient using at least one infusion, preferably at least two or more separate infusions.

The NK-92 cells of the invention can be used for functional analysis of TCRs, both in vitro and in vivo using preclinical animal models such as NSG xenograft models. Furthermore, TCRs with unknown specificity can be expressed in the modified NK-92 cells along with CD3 and CD4/CD8 in order to screen antigen libraries. For example, HEK cells that carry the corresponding MHC restriction element or cDNA pools derived from AML blastocysts can be used. As such, the modified NK-92 cells of the present invention are suitable for in vitro diagnosis, in vitro diagnostics and/or in vitro screening.

In a further aspect of the invention, the modified NK-92 cell is also suitable for targeting virally infected cells, in particular cells that are infected with a pathogenic virus such as CMV, EBV, HPV, HBV, HCV, HHV-8, HTLV-1, SARS-CoV-2, MCV, MCPyV, SV-40, or HIV.

The present invention also relates to an expression vector or an expression construct, such as a plasmid or other genetic vehicle, comprising the nucleic acid sequences of an antigen-specific functional TCR, CD3, CD4 and/or CD8. In a preferred embodiment, the vector comprises nucleic acid sequences derived from any of the nucleic acid sequences defined in SEQ ID NO: 1 to 12 for expressing TCR, CD3, CD4 and/or CD8.

The present invention also relates to in vitro methods for the preparation of a modified NK-92 cell that is specific for target antigen of a target cell in a subject. The method comprises:

(1) determining a target antigen in the target cell that is expressed on the surface of the target cell,
(2) identifying the type of the MHC complex in the subject,
(3) providing a NK-92 cell that expresses
   i. an antigen-specific T cell receptor (TCR) that has the ability of specifically binding to the antigen-MHC complex identified in step (1) on the surface of the target cell,
   ii. CD3.
   iii. CD4 and/or CD8 to produce a NK-92-TCR-CD3$^+$-CD4$^+$ cell or NK-92-TCR-CD3$^+$-CD8$^+$ or NK-92-TCR-CD3$^+$-CD4$^+$-CD8$^+$ cell.

The TCR utilized can be any TCR that comprises a TCR-recognition domain that selectively binds to an antigen on the surface of a target cell. Any native or non-native TCR can be used, both of natural, synthetic or artificial origin, including but not limited to TCR constructs, variants or derivatives thereof.

An NK-92-TCR-CD3$^+$-CD4$^+$/CD8$^+$ cell of the present invention is highly antigen-specific and exhibits a high cytotoxic activity towards the target cell. In general, the specificity of the NK-92 cell is determined by the specificity of the TCR. However, the desired specificity can be influenced by co-expression of CD3 and CD4 and/or CD8. Preferably, the TCR is capable of binding to MHC-antigen complex on the surface of a target cell with high affinity.

The inventors generated several plasmids to infect NK-92 cells in order to express TCR-CD3-CD4 or TCR-CD3-CD8. In order to connect two genes in the peptide-based multigene expression system, self-cleaving 2A peptide sequences of viral origins have been used, e.g. P2A, T2A, E2A, F2A.

The following nucleic acid sequences are examples of CD8 transcripts that can be used to transfect NK-92 cells.

8

CD8α transcript 1
(SEQ ID NO: 7)
5'-GCCACCATGGCCTTACCAGTGACCGCCTT

GCTCCTGCCGCTGGCCTTGCTGCTCCACGCCGCCA

GGCCGAGCCAGTTCCGGGTGTCGCCGCTGGATCGG

ACCTGGAACCTGGGCGAGACAGTGGAGCTGAAGTG

CCAGGTGCTGCTGTCCAACCCGACGTCGGGCTGCT

CGTGGCTCTTCCAGCCGCGCGGCGCCGCCGCCAGT

CCCACCTTCCTCCTATACCTCTCCCAAAACAAGCC

CAAGGCGGCCGAGGGGCTGGACACCCAGCGGTTCT

CGGGCAAGAGGTTGGGGGACACCTTCGTCCTCACC

CTGAGCGACTTCCGCCGAGAGAACGAGGGCTACTA

TTTCTGCTCGGCCCTGAGCAACTCCATCATGTACT

TCAGCCACTTCGTGCCGGTCTTCCTGCCAGCGAAG

CCCACCACGACGCCAGCGCCGCGACCACCAACACC

GGCGCCCACCATCGCGTCGCAGCCCCTGTCCCTGC

GCCCAGAGGCGTGCCGGCCAGCGGCGGGGGGCGCA

GTGCACACGAGGGGGCTGGACTTCGCCTGTGATAT

CTACATCTGGGCGCCCCTGGCCGGGACTTGTGGGG

TCCTTCTCCTGTCACTGGTTATCACCCTTTACTGC

AACCACAGGAACCGAAGACGTGTTTGCAAATGTCC

CCGGCCTGTGGTCAAATCGGGAGACAAGCCCAGCC

TTTCGGCGAGATACGTC-3'

CD8α transcript 2
(SEQ ID NO: 8)
5'-GCCACCATGGCCTTACCAGTGACCGCCTTGCTCCT

GCCGCTGGCCTTGCTGCTCCACGCCGCCAGGCCGA

GCCAGTTCCGGGTGTCGCCGCTGGATCGGACCTGG

AACCTGGGCGAGACAGTGGAGCTGAAGTGCCAGGT

GCTGCTGTCCAACCCGACGTCGGGCTGCTCGTGGC

TCTTCCAGCCGCGCGGCGCCGCCGCCGCCAGTCCCACC

TTCCTCCTATACCTCTCCCAAAACAAGCCCAAGGC

GGCCGAGGGGCTGGACACCCAGCGGTTCTCGGGCA

AGAGGTTGGGGGACACCTTCGTCCTCACCCTGAGC

GACTTCCGCCGAGAGAACGAGGGCTACTATTTCTG

CTCGGCCCTGAGCAACTCCATCATGTACTTCAGCC

ACTTCGTGCCGGTCTTCCTGCCAGCGAAGCCCACC

ACGACGCCAGCGCCGCGACCACCAACACCGGCGCC

CACCATCGCGTCGCAGCCCCTGTCCCTGCGCCCAG

AGGCGTGCCGGCCAGCGGCGGGGGGCGCAGGGAAC

CGAAGACGTGTTTGCAAATGTCCCCGGCCTGTGGT

CAAATCGGGAGACAAGCCCAGCCTTTCGGCGAGAT

-continued

ACGTC-3'

CD8β transcript 2

(SEQ ID NO: 9)

5'-
CTCCAGCAGACCCCTGCATACATAAAGGTGCAAAC

CAACAAGATGGTGATGCTGTCCTGCGAGGCTAAAA

TCTCCCTCAGTAACATGCGCATCTACTGGCTGAGA

CAGCGCCAGGCACCGAGCAGTGACAGTCACCACGA

GTTCCTGGCCCTCTGGGATTCCGCAAAAGGGACTA

TCCACGGTGAAGAGGTGGAACAGGAGAAGATAGCT

GTGTTTCGGGATGCAAGCCGGTTCATTCTCAATCT

CACAAGCGTGAAGCCGGAAGACAGTGGCATCTACT

TCTGCATGATCGTCGGGAGCCCCGAGCTGACCTTC

GGGAAGGGAACTCAGCTGAGTGTGGTTGATTTCCT

TCCCACCACTGCCCAGCCCACCAAGAAGTCCACCC

TCAAGAAGAGAGTGTGCCGGTTACCCAGGCCAGAG

ACCCAGAAGGGCCCACTTTGTAGCCCCATCACCCT

TGGCCTGCTGGTGGCTGGCATCCTGGTTCTGCTGG

TTTCCCTGGGAGTGGCCATCCACCTGTGCTGCCGG

CGGAGGAGAGCCCGGCTTCGTTTCATGAAACAGCC

TCAAGGGGAAGGTGTATCAGGAACCTTTGTCCCCC

AATGCCTGCATGGATACTACAGCAATACTACAACC

TCACAGAAGCTGCTTAACCCATGGATCCTGAAAAC

ATAG-3'

CD8β transcript 3

(SEQ ID NO: 10)

5'-CTCCAGCAGACCCCTGCATACATAAAGGT

GCAAACCAACAAGATGGTGATGCTGTCCTGCGAGG

CTAAAATCTCCCTCAGTAACATGCGCATCTACTGG

CTGAGACAGCGCCAGGCACCGAGCAGTGACAGTCA

CCACGAGTTCCTGGCCCTCTGGGATTCCGCAAAAG

GGACTATCCACGGTGAAGAGGTGGAACAGGAGAAG

ATAGCTGTGTTTCGGGATGCAAGCCGGTTCATTCT

CAATCTCACAAGCGTGAAGCCGGAAGACAGTGGCA

TCTACTTCTGCATGATCGTCGGGAGCCCCGAGCTG

ACCTTCGGGAAGGGAACTCAGCTGAGTGTGGTTGA

TTTCCTTCCCACCACTGCCCAGCCCACCAAGAAGT

CCACCCTCAAGAAGAGAGTGTGCCGGTTACCCAGG

CCAGAGACCCAGAAGGGCCCACTTTGTAGCCCCAT

CACCCTTGGCCTGCTGGTGGCTGGCGTCCTGGTTC

TGCTGGTTTCCCTGGGAGTGGCCATCCACCTGTGC

TGCCGGCGGAGGAGAGCCCGGCTTCGTTTCATGAA

ACAACTAAGATTACATCCACTGGAGAAATGTTCCA

-continued

GAATGGACTACTGA-3'

CD8β transcript 5

(SEQ ID NO: 11)

5'-CTCCAGCAGACCCCTGCATACATAAAGGTG

CAAACCAACAAGATGGTGATGCTGTCCTGCGAGGC

TAAAATCTCCCTCAGTAACATGCGCATCTACTGGC

TGAGACAGCGCCAGGCACCGAGCAGTGACAGTCAC

CACGAGTTCCTGGCCCTCTGGGATTCCGCAAAAGG

GACTATCCACGGTGAAGAGGTGGAACAGGAGAAGA

TAGCTGTGTTTCGGGATGCAAGCCGGTTCATTCTC

AATCTCACAAGCGTGAAGCCGGAAGACAGTGGCAT

CTACTTCTGCATGATCGTCGGGAGCCCCGAGCTGA

CCTTCGGGAAGGGAACTCAGCTGAGTGTGGTTGAT

TTCCTTCCCACCACTGCCCAGCCCACCAAGAAGTC

CACCCTCAAGAAGAGAGTGTGCCGGTTACCCAGGC

CAGAGACCCAGAAGGGCCCACTTTGTAGCCCCATC

ACCCTTGGCCTGCTGGTGGCTGGCGTCCTGGTTCT

GCTGGTTTCCCTGGGAGTGGCCATCCACCTGTGCT

GCCGGCGGAGGAGAGCCCGGCTTCGTTTCATGAAA

CAATTTTACAAATGA-3'

CD3 construct (SEQ ID NO: 12)

An example of a CD3 construct that can be expressed in a modified NK cell, preferably a NK-92 cell is disclosed in SEQ ID NO: 12. The sequence of the CD3 construct comprises the sequences for δ, γ, ε and ζ. The bold letters mark the 2A self-cleaving peptide sequences.

5'ATATATACAAGGACAAAGAATCTACCGTGCAAG

TTCATTATCGAATGTGCCAGAGCTGTGTGGAGCTG

GATCCAGCCACCGTGGCTGGCATCATTGTCACTGA

TGTCATTGCCACTCTGCTCCTTGCTTTGGGAGTCT

TCTGCTTTGCTGGACATGAGACTGGAAGGCTGTCT

GGGGCTGCCGACACACAAGCTCTGTTGAGGAATGA

CCAGGTCTATCAGCCCCTCCGAGATCGAGATGATG

CTCAGTACAGCCACCTTGGAGGAAACTGGGCTCGG

AACAAGGGACCGGTGAAACAGACTTTGAATTTTGA

CCTTCTCAAGTTGGCGGGAGACGTGGAGTCCAACC

CAGGGCCCATGGAACAGGGGAAGGGCCTGGCTGTC

CTCATCCTGGCTATCATTCTTCTTCAAGGTACTTT

GGCCCAGTCAATCAAAGGAAACCACTTGGTTAAGG

TGTATGACTATCAAGAAGATGGTTCGGTACTTCTG

ACTTGTGATGCAGAAGCCAAAAATATCACATGGTT

TAAAGATGGGAAGATGATCGGCTTCCTAACTGAAG

-continued

```
ATAAAAAAAAATGGAATCTGGGAAGTAATGCCAAG

GACCCTCGAGGGATGTATCAGTGTAAAGGATCACA

GAACAAGTCAAAACCACTCCAAGTGTATTACAGAA

TGTGTCAGAACTGCATTGAACTAAATGCAGCCACC

ATATCTGGCTTTCTCTTTGCTGAAATCGTCAGCAT

TTTCGTCCTTGCTGTTGGGGTCTACTTCATTGCTG

GACAGGATGGAGTTCGCCAGTCGAGAGCTTCAGAC

AAGCAGACTCTGTTGCCCAATGACCAGCTCTACCA

GCCCCTCAAGGATCGAGAAGATGACCAGTACAGCC

ACCTTCAAGGAAACCAGTTGAGGAGGAATAGAAGA

TCTGAGGGCAGAGGAAGTCTGCTAACATGCGGTGA

CGTCGAGGAGAATCCTGGCCCAATGCAGTCGGGCA

CTCACTGGAGAGTTCTGGGCCTCTGCCTCTTATCA

GTTGGCGTTTGGGGGCAAGATGGTAATGAAGAAAT

GGGTGGTATTACACAGACACCATATAAAGTCTCCA

TCTCTGGAACCACAGTAATATTGACATGCCCTCAG

TATCCTGGATCTGAAATACTATGGCAACACAATGA

TAAAAACATAGGCGGTGATGAGGATGATAAAAACA

TAGGCAGTGATGAGGATCACCTGTCACTGAAGGAA

TTTTCAGAATTGGAGCAAAGTGGTTATTATGTCTG

CTACCCCAGAGGAAGCAAACCAGAAGATGCGAACT

TTTATCTCTACCTGAGGGCAAGAGTGTGTGAGAAC

TGCATGGAGATGGATGTGATGTCGGTGGCCACAAT

TGTCATAGTGGACATCTGCATCACTGGGGGCTTGC

TGCTGCTGGTTTACTACTGGAGCAAGAATAGAAAG

GCCAAGGCCAAGCCTGTGACACGAGGAGCGGGTGC

TGGCGGCAGGCAAAGGGGACAAAACAAGGAGAGGC

CACCACCTGTTCCCAACCCAGACTATGAGCCCATC

CGGAAAGGCCAGCGGGACCTGTATTCTGGCCTGAA

TCAGAGACGCATCGGAGGATCCGCCACGAACTTCT

CTCTGTTAAAGCAAGCAGGAGACGTGGAAGAAAAC

CCCGGTCCCATGAAGTGGAAGGCGCTTTTCACCGC

GGCCATCCTGCAGGCACAGTTGCCGATTACAGAGG

CACAGAGCTTTGGCCTGCTGGATCCCAAACTCTGC

TACCTGCTGGATGGAATCCTCTTCATCTATGGTGT

CATTCTCACTGCCTTGTTCCTGAGAGTGAAGTTCA

GCAGGAGCGCAGACGCCCCCGCGTACCAGCAGGGC

CAGAACCAGCTCTATAACGAGCTCAATCTAGGACG

AAGAGAGGAGTACGATGTTTTGGACAAGAGACGTG

GCCGGGACCCTGAGATGGGGGGAAAGCCGAGAAGG
```

-continued

```
AAGAACCCTCAGGAAGGCCTGTACAATGAACTGCA

GAAAGATAAGATGGCGGAGGCCTACAGTGAGATTG

GGATGAAAGGCGAGCGCCGGAGGGGCAAGGGGCAC

GATGGCCTTTACCAGGGTCTCAGTACAGCCACCAA

GGACACCTACGACGCCCTTCACATGCAGGCCCTGC

CCCCTCGCTAA 3'
```

MODES FOR CARRYING OUT THE INVENTION

The invention will be explained in more detail in the following examples. By no means shall the invention be limited to these examples.

EXAMPLES

Cloning of the constructs encoding for TCR, CD3, CD8 was performed using the plasmids shown in FIGS. 1 to 7.

Example 1: Expression of Human CD3 Complex in NK92 Cells

Codon-optimized genes for the delta, gamma, epsilon and zeta chain of the human CD3 complex were cloned into the pMXs_IRES_Puromycin vector (pMXs_IRES_Puro_CD3) connected to each other via different 2A-self cleaving peptide sequences. GALV pseudotyped retroviral particles containing the CD3 construct were obtained following transfection of HEK-Phoenix-Ampho cells and used to retrovirally transduce NK92 cells by spin infection in the presence of polybrene. As the CD3 complex and αβ-TCR require each other for cell surface expression, successful transduction of NK92 cells with CD3 (NK92CD3$^+$) was confirmed following puromycin selection and additional retroviral gene transfer of 3 different T cell receptors (TCR) (5H11, 25F2, 5B2) by flow cytometry using a FACS Canto II flow cytometer (BD Biosciences). Upon antibiotic selection at least 86% of CD3$^+$ NK92 cells expressing CD3 in combination with a given TCR were obtained (see FIG. 8).

Example 2: Expression of CD8 in NK92 Cells

For expression of CD8 in NK92 cells, total cDNA was extracted from the original cytotoxic T lymphocyte (CTL) clones 5B2 and 25F2. PCR was then performed to isolate the α1 and α2 chains of human CD8 as well as the β2, β3, and β5 isoforms of human CD8 (see SEQ ID NO: 7 to 11). Different combinations of CD8 α- and ß-chains (e.g. α1/β2, α1/β5, α2/β3) were cloned into pMXs_IRES-Neomycin (pMXs_IRES_Neo_CD8) using the P2A self-cleavage peptide sequence to express both α and β chains, and retroival particles were produced in HEK-Phoenix-Ampho cells as described above. Following retroviral gene transfer of different CD8 combinations into NK92CD3$^+$ cells and neomycin/puromycin selection at least 90% of NK92CD3$^+$ cells also expressed one of the different CD8αβ combinations as measured by flow cytometry and exemplarily shown for 96.8% of NK92CD3$^+$ cells expressing CD8α1β2 (FIG. 9).

Example 3: Cloning of TCRs 5B2, 25F2 and 5H11

The TCRs 5H11 (Vβ8), 25F2 (Vβ8) and 5B2 (Vβ21.3) utilized for expression in NK92CD3$^+$ and NK92CD3$^+$CD8$^+$ cells were originally derived from AML-specific cytotoxic CD8$^+$ CTL clones by PCR cloning. The clones 5B2 and 25F2 were previously shown to recognize patient-derived AML blasts while the CTL 5H11 exerted reactivity to both AML and EBV-transformed B cells (B-LCL) from the same patient but not to fibroblasts indicating that this TCR might recognize a hematopoiesis-specific minor-histocompatibility antigen whereas 5B2 and 25F2 presumably recognize AML-associated or AML-specific antigens. TCR expression could be detected by FITC- or PE-labeled TCRβ-chain specific monoclonal antibodies (mAb) reactive to Vβ8 (5H11 and 25F2) and Vß21.3 (5B2). Codon optimized and constant domain murinized α- and β-sequences of each TCR (SEQ ID NOs 1-6) were cloned into the pMXs_IRES_Puromycin vector connected by a P2A sequence.

Example 4: Expression of the TCRs 5B2, 25F2 and 5H11 in NK92CD3$^+$CD8$^+$ Cells Established NK92CD3$^+$CD8$^+$ transfectants were retrovirally transduced with the 3 different TCRs to study TCR-CD3-CD8 co-expression. Following retroviral gene transfer TCR and CD3/CD8 co-expression was initially examined by flow cytometry 48 h after transduction using the corresponding FITC- or PE-labeled anti-TCR-Vβ mAb, an anti-CD3 mAb labeled either with Pacific-Blue or APC and an anti-CD8 mAb conjugated to PE or APC. As shown exemplarily for NK92CD3$^+$CD8α1β2$^+$ cells expression of TCRβ, CD3 and CD8 was examined by flow cytometry and cells expressing TCR/CD3 or TCR/CD3/CD8 appear in the upper right quadrant of the dot plots depicted. Following 2-3 cycles of either fluorescence activated cell sorting (FACS®) and/or immunomagnetic cell sorting (MACS®) at least 80% of NK92CD3$^+$CD8$^+$ cells could be shown to express the TCRs 5H11 (FIG. 10A, B), 25F2 (FIG. 11A, B) and 5B2 (FIG. 12A, B) whereas non TCR transduced NK92CD3$^+$ CD8$^+$ cells lacked TCR expression examined by CD3 and CD8 staining (FIG. 10C, 11C, 12C) as the TCR is required for expression of the CD3 complex.

Example 5: NK92CD3$^+$CD8$^+$ Cells Expressing TCR are Functional

To validate function following TCR expression 1×10$^5$ redirected 5B2-CD3$^+$CD8$^+$ NK92-, 25F2-CD3$^+$CD8$^+$ NK92-, and 5H11-CD3$^+$CD8$^+$ NK92 effector cells were cocultured overnight with 1×10$^5$ HLA-matched, patient-derived (primary) AML blasts and/or B-LCL expressing the appropriate MHC class I restriction allele, and IFN-γ release was examined in an IFN-γ ELISPOT assay. Non HLA-matched AML blasts or B-LCL as well as K562 served as specificity controls.

All TCR redirected NK92CD3$^+$CD8$^+$ populations elicited profound IFN-γ release upon stimulation with MHC-matched AML blasts (FIGS. 13 to 15). In contrast, non TCR transduced NK92CD3$^+$ included as controls exerted only basal non-specific responses to AML blasts.

Moreover, significant IFN-γ release of TCR 5H11 expressed in 5H11CD3$^+$ NK92 and 5H11CD3$^+$CD8$^+$ NK92 could only be observed in the presence of CD8 demonstrating that the generated NK92CD3$^+$CD8$^+$ cells are well suitable to test whether a given TCR derived from a CD8$^+$ CTL clone is CD8 dependent or CD8 independent.

In addition to IFN-γ release, direct cytolytic activity of TCR-redirected NK92CD3$^+$CD8$^+$ cells was determined using a bioluminescence (BLI)-based cytotoxicity assay. Since the TCR 5H11 recognizes both HLA-matched AML blasts and EBV-immortalized human B cells (B-LCL) from the same patient, FLuc-expressing B-LCL transfectants were established by lentiviral gene transfer and used as targets for 5H11CD3$^+$CD8$^+$ NK92 effector cells. Unfortunately, no FLuc transfectants of AML could be established as primary AML blasts do not grow in vitro.

Next, 5H11CD3$^+$CD8$^+$ NK92 and FLuc-expressing B-LCL were co-incubated in triplicates at the indicated effector:target ratios in the presence of D-Luciferin for 18 hours. TCR 5B2 positive NK92CD3$^+$CD8$^+$ cells were used as specificity control. BLI was measured as relative light units (RLU) 18 hours after co-cultivation and TCR-specific lysis was determined relative to BLI reduction of target cells co-cultured with non TCR transduced NK92CD3$^+$. NK-cell mediated cytotoxicity of NK92CD3$^+$ against EBV-B 580 never exceeded 10% killing.

As demonstrated in FIG. 16, 5H11CD3$^+$CD8$^+$ NK92 elicited robust cytotoxicity to FLuc$^+$ B-LCL from patient MZ580, and this response was strictly CD8 dependent confirming the IFN-γ release data (FIG. 13). Moreover, 5B2CD3$^+$CD8$^+$ NK92 effectors did not exert any reactivity, strongly suggesting that the cytolytic activity observed was TCR-mediated.

Intriguingly, co-culture of TCR 5H11 and TCR 5B2 redirected NK92CD3$^+$ as well as NK92CD3$^+$CD8$^+$ cells with FLuc-expressing K562 target cells at an E:T ratio of 10:1 revealed strong cytolytic responses by TCR negative (but CD3 transduced) NK92 cells to HLA class I and II negative K562 targets within the first 5 hours whereas cytotoxicity by both TCR 5H11 and 5B2 redirected NK92CD3$^+$ and NK92CD3$^+$CD8$^+$ was diminished. Upon 24 hours of co-incubation overall cytolytic activity by both TCR negative and TCR positive NK cell subsets reached 100% thereby masking the observed differences in reactivity. These data strongly suggest that intrinsic NK-cell mediated cytotoxicity is downregulated in the presence of transgenic TCR expression. In addition, this downregulation of innate immune function requires a functional TCR complex such as additional expression of the CD8 co-receptor since reduction of innate immunity was not observed for 5H11CD3$^+$ but 5H11CD3$^+$CD8$^+$ NK92 cells (FIG. 17A). In contrast, this effect was not observed for 5B2CD3$^+$ and 5B2CD3$^+$CD8$^+$ NK92 cells (FIG. 17B) suggesting CD8 independence of TCR 5B2 in line with the results obtained in FIG. 15.

In summary, these results demonstrate that NK92CD3$^+$ and NK92CD3$^+$CD8$^+$ expressing AML reactive TCRs are able to elicit robust, TCR-mediated, anti-tumoural responses as measured by IFN-γ release and direct cytotoxicity. Moreover, NK92CD3$^+$CD8$^+$ cells can be used to examine co-receptor dependence of TCRs derived from CD8$^+$ CTL clones.

Example 6: Analysis of NK92 Marker Expression on Genetically Modified NK92 Cells Expression profiles of activating (NKp30, NKp44, NKG2C, NKG2D) and inhibiting receptors (NKG2A, TIGIT, CD96, TIM-3, CTLA4, PD1) commonly expressed on NK cells were compared between NK92 wt, TCR-redirected NK92CD3$^+$ and TCR-CD3$^+$CD8$^+$ NK92 cells as shown in FIG. 18 for 5H115B2CD3$^+$CD8$^+$ NK92 and 5B2CD3$^+$CD8$^+$ NK92 cells. While no significant changes were observed for all inhibiting markers examined among the five subsets of cells as measured by flow cytometry using marker-specific Abs (FIG. 18), expression of the activating natural cytotoxicity receptor (NCR) NKp30 was found to be reduced in NK92CD3$^+$ cells upon expression of a TCR (FIG. 18). This effect was more pronounced in the TCR-redirected NK92CD3$^+$CD8$^+$ subset. In addition, we also observed reduced expression levels of the activating NCR NKG2D on TCR-redirected NK92CD3$^+$ and NK92CD3$^+$ CD8$^+$ cells, suggesting that TCR expression in NK92 cells results in downregulation of activating NCR expression and subsequently reduced NCR-mediated function of NK92 cells. Of note, these data are in line with the results described in Example 5 on innate immune responses of TCR-redirected NK92 cells to K562 targets. Thus, expression of a functional TCR complex in NK92 cells might reduce non-specific innate immunity while promoting TCR-driven reactivity.

Figure 1:
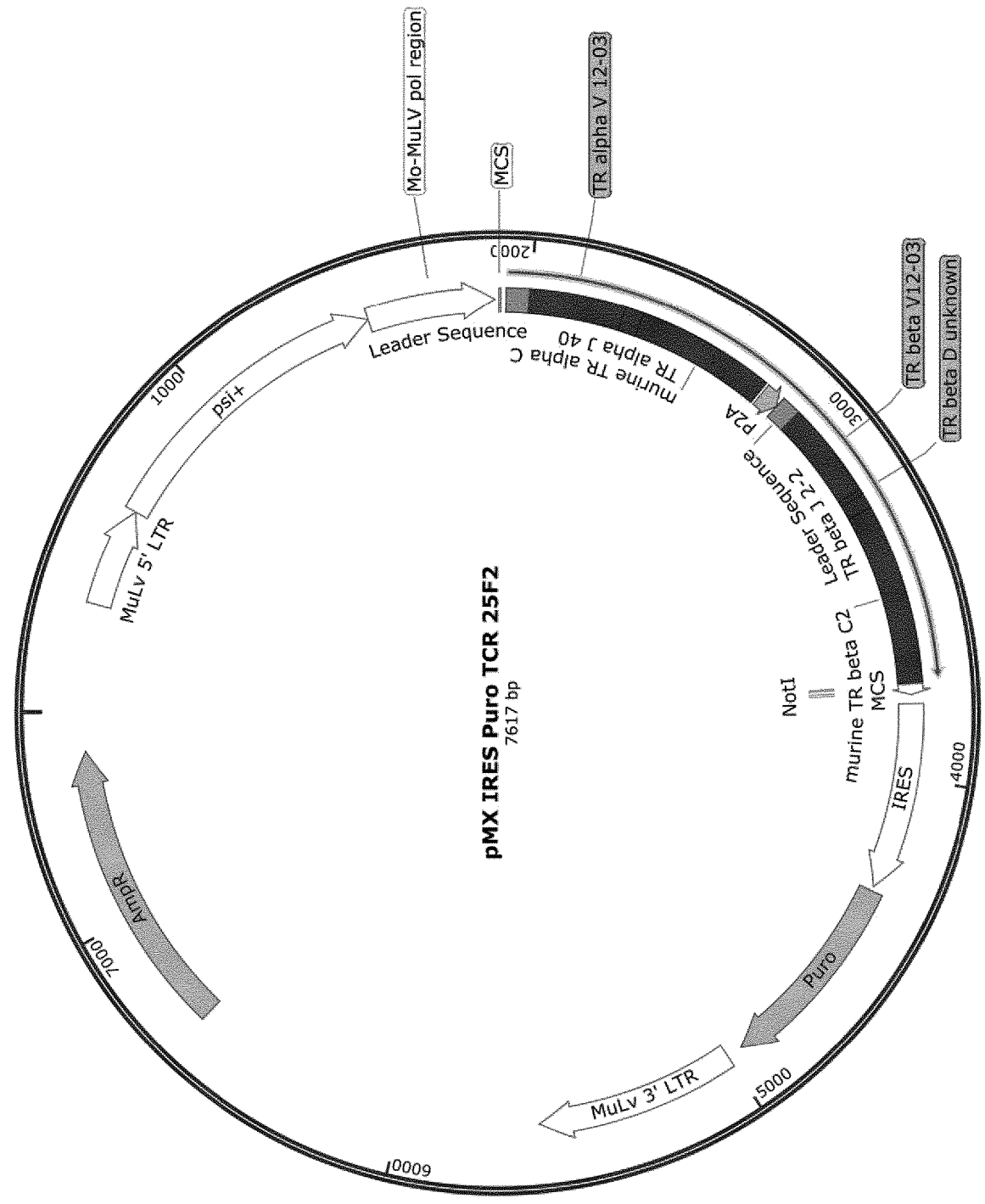
FIG. 1 shows the gene card of plasmid pMX_IRES_Puro_TCR-25F2
Figure 2:
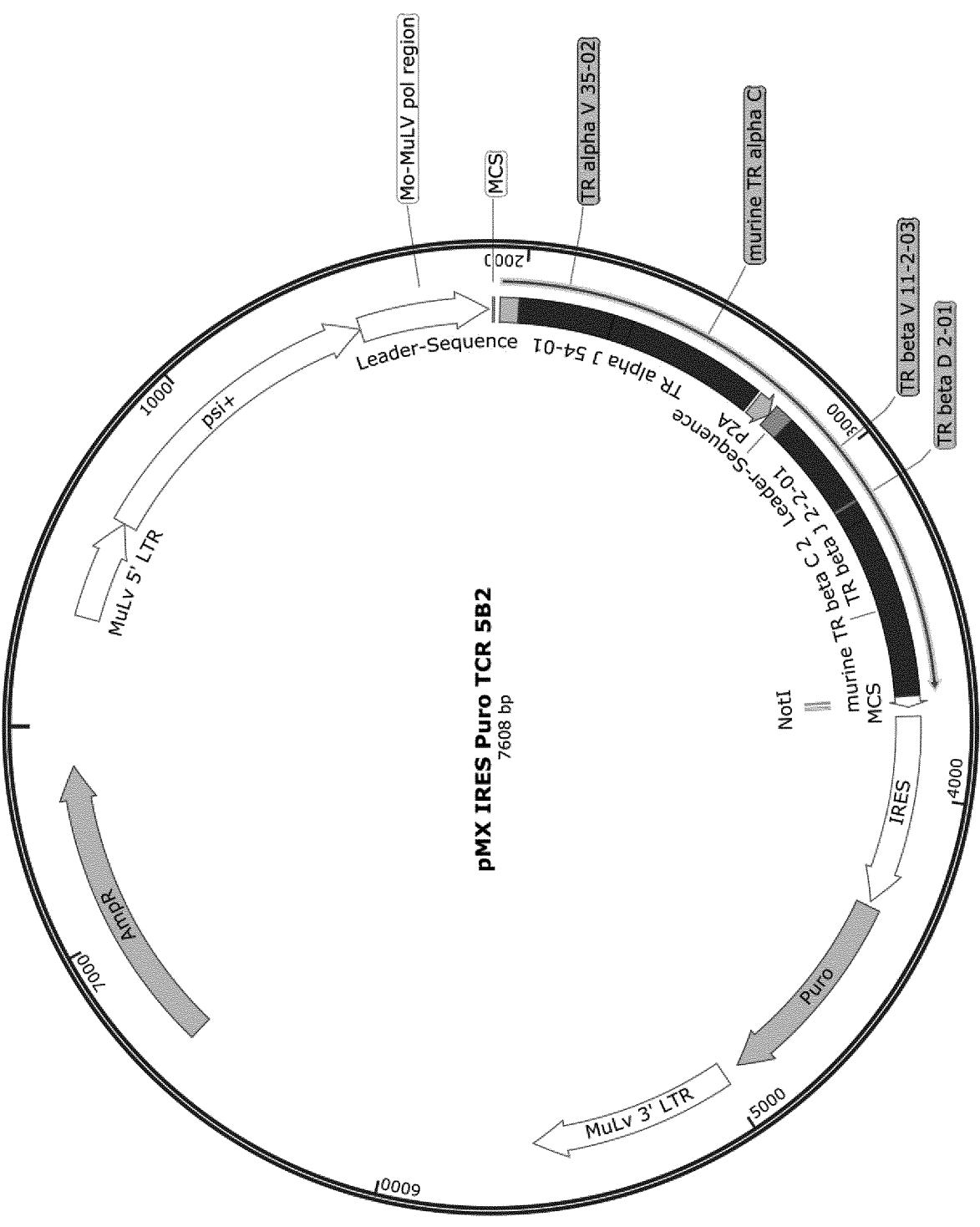
FIG. 2 shows the gene card of plasmid pMX_IRES_Puro_TCR-562
Figure 3:
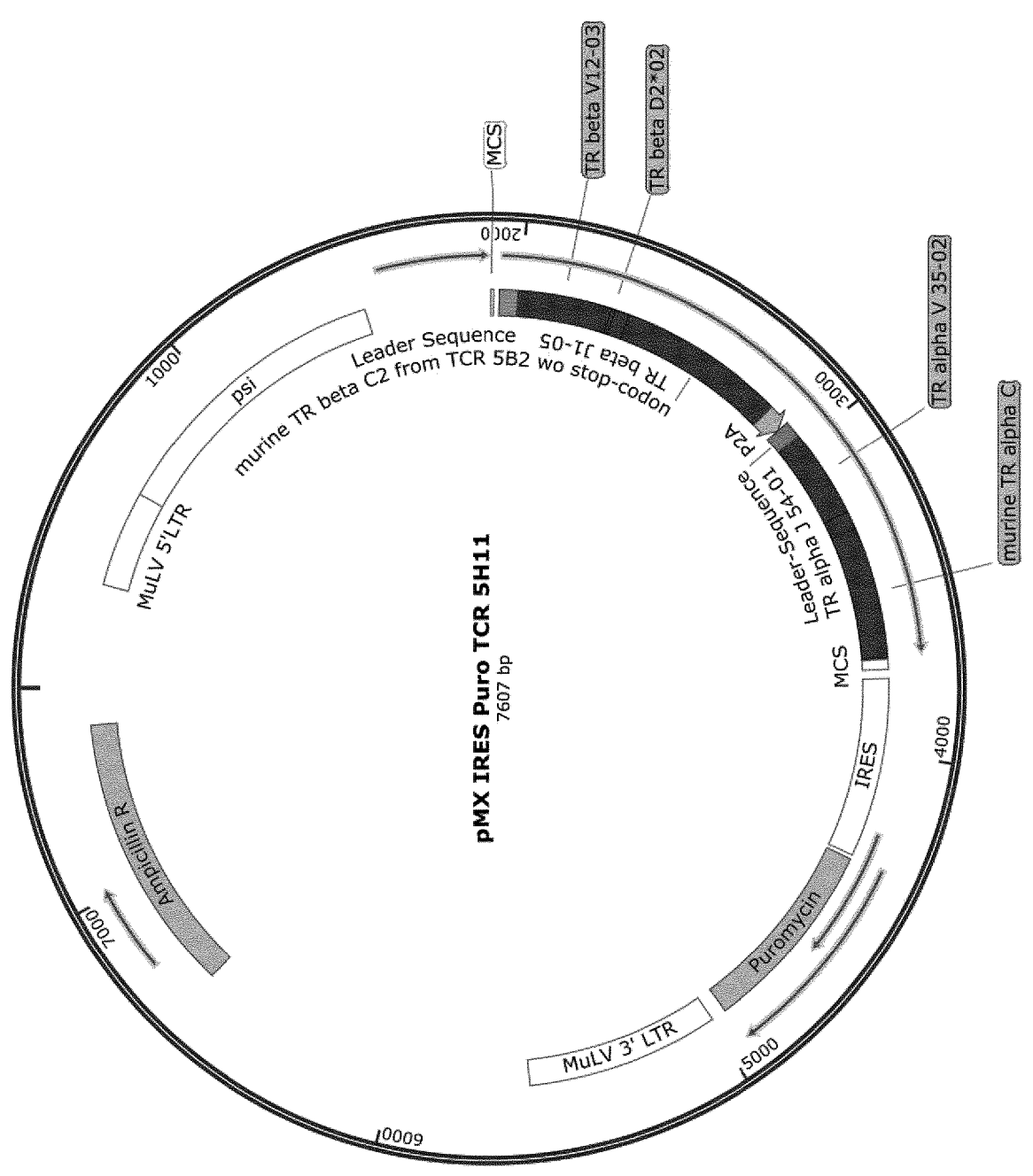
FIG. 3 shows the gene card of plasmid pMX_IRES_Puro_TCR-5H11
Figure 4:
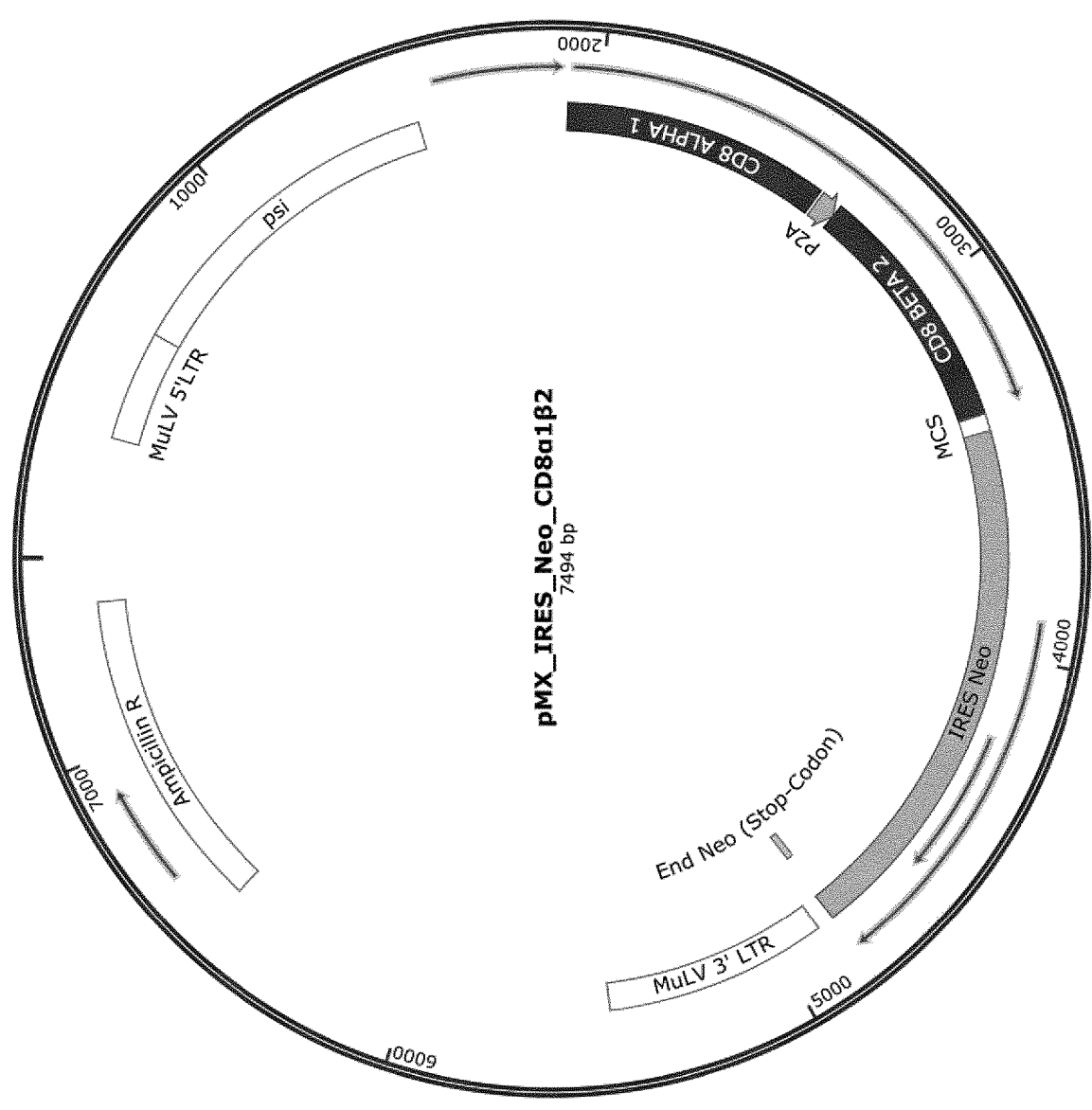
FIG. 4 shows the gene card of plasmid pMX_IRES_Neo_CD8α1β2
Figure 5:
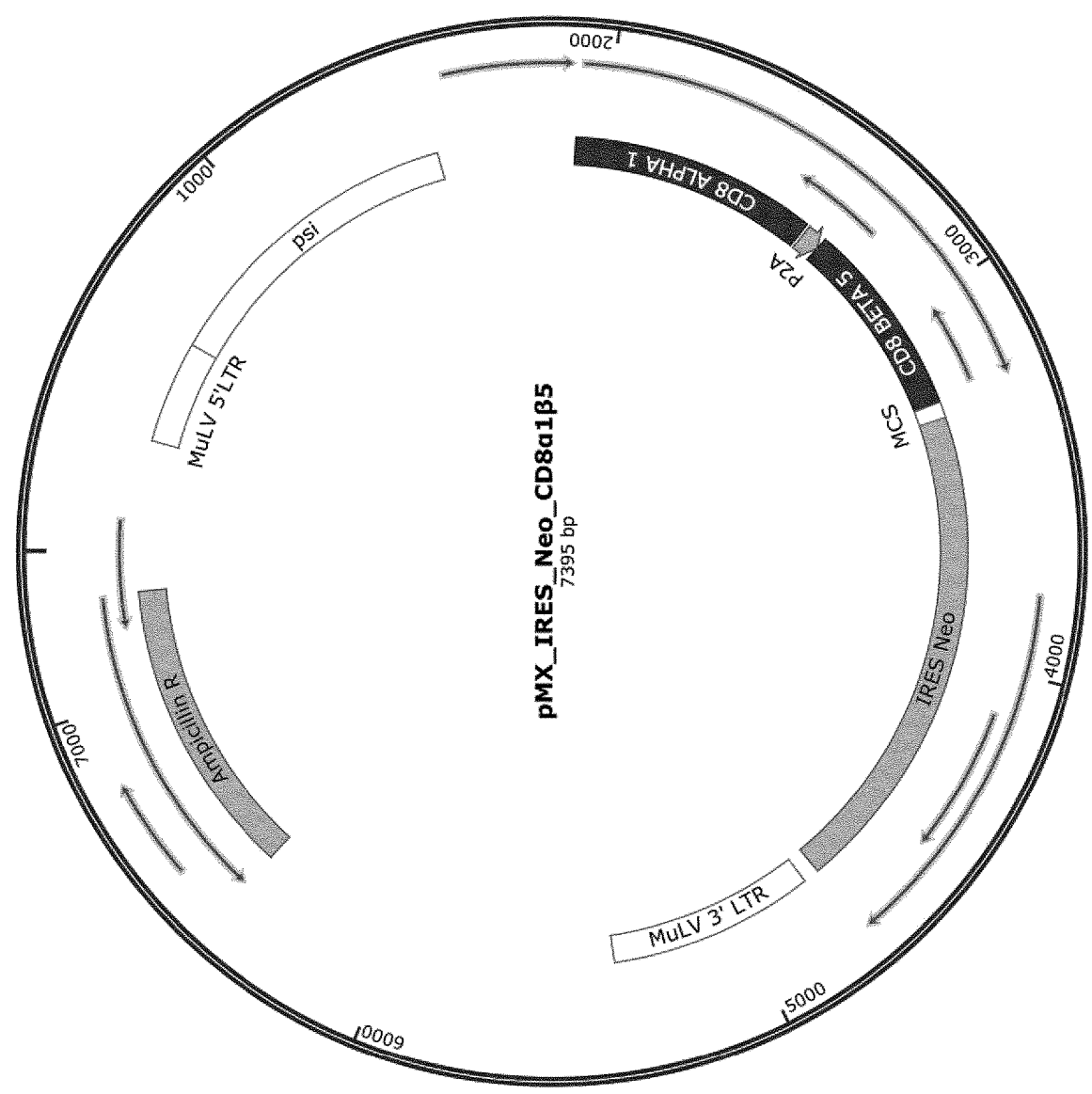
FIG. 5 shows the gene card of plasmid pMX_IRES_Neo_CD8α1β5
Figure 6:
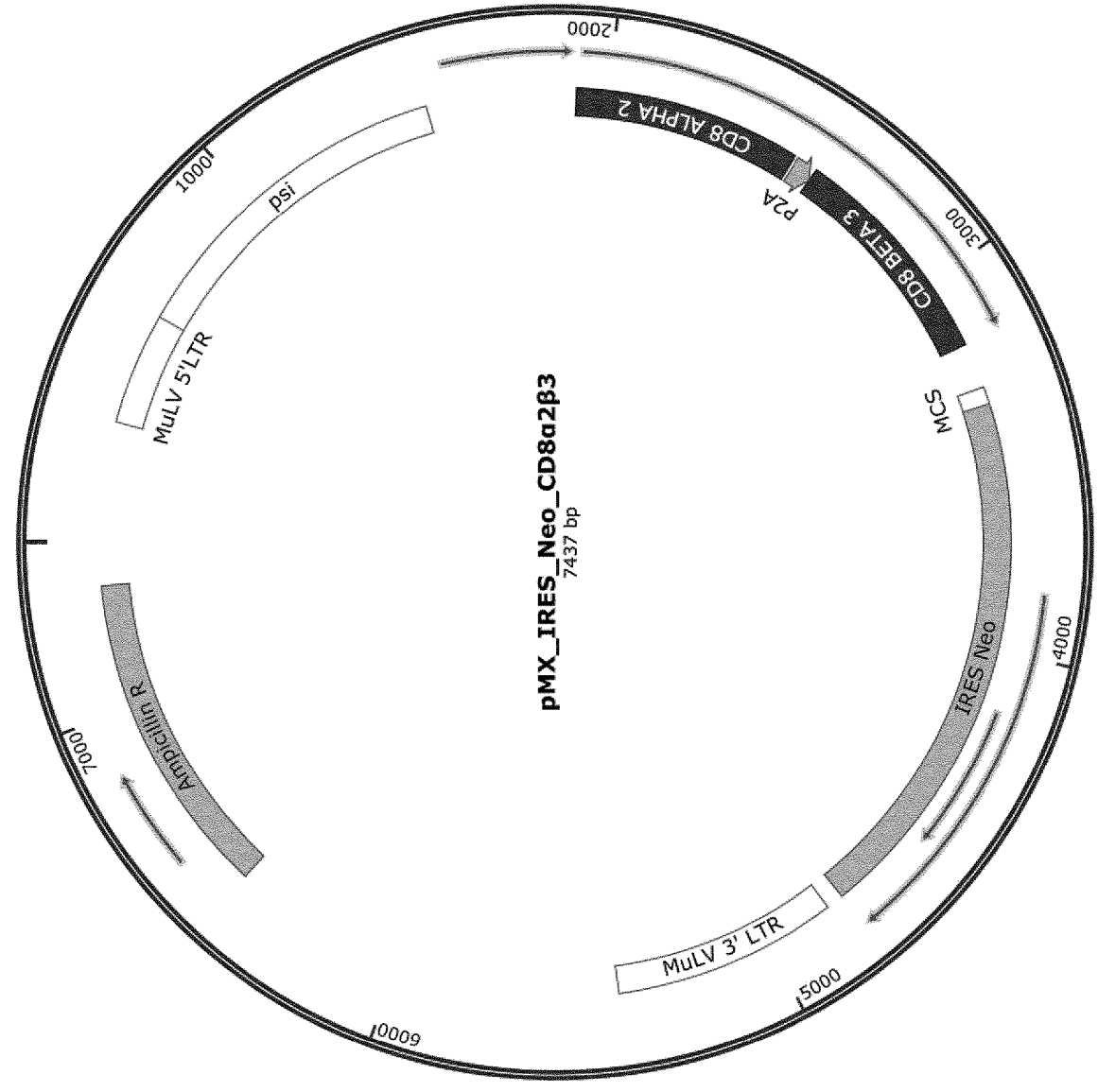
FIG. 6 shows the gene card of plasmid pMX_IRES_Neo_CD8α2β3
Figure 7:
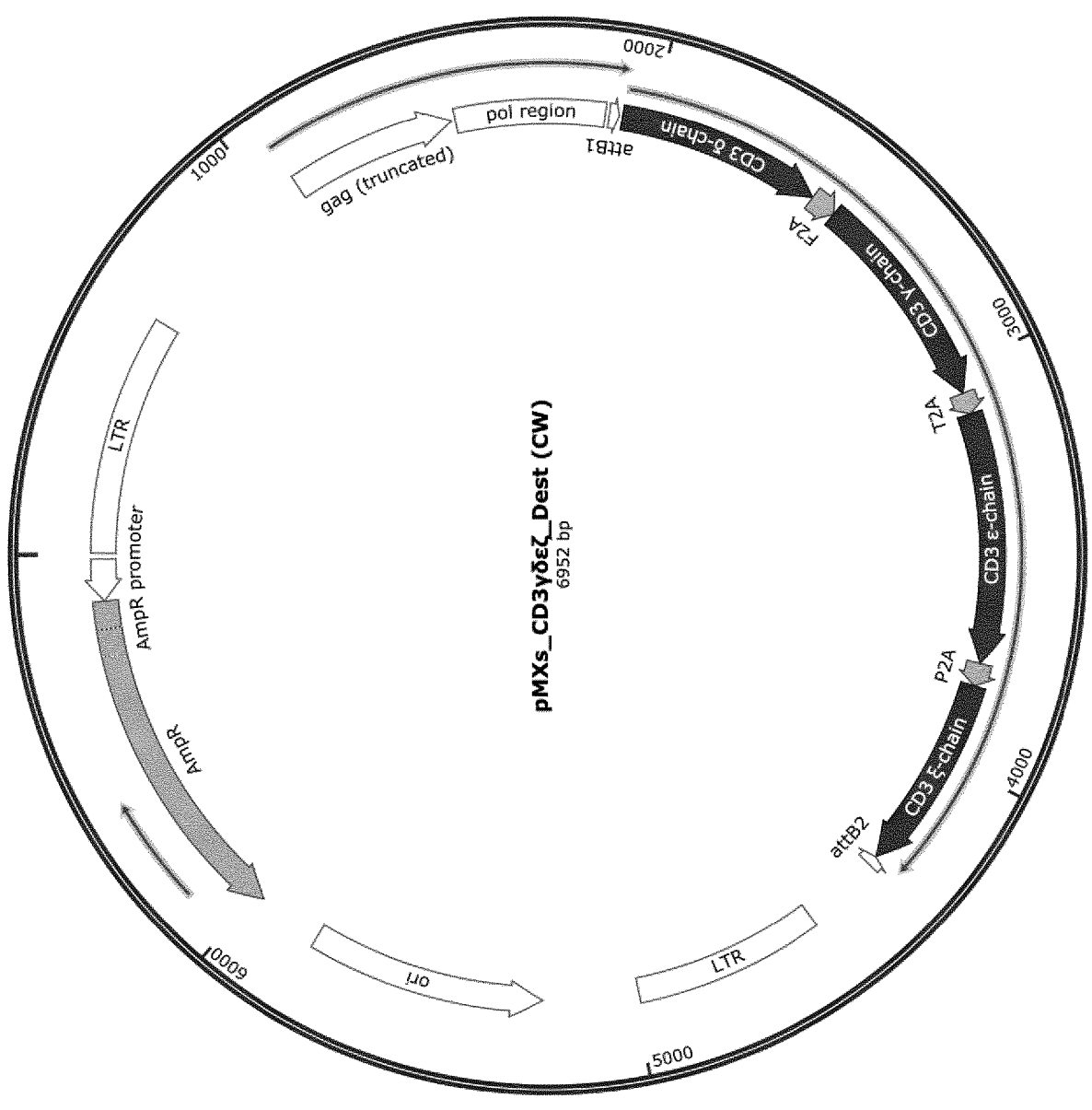
FIG. 7 shows the gene card of plasmid pMXs_CD3 complex_Dest. The genes encoding for the CD3δ-, CD3γ-, CD3ε- and CD3ζ-chain, connected to each other by insertion of sequences coding for the F2A, T2A, and P2A self-cleaving peptides were cloned into a pMXs-based destination vector modified for Gateway-Cloning®. The CD3 complex was then finally transferred into the retroviral pMXs_IRES_Puromycin vector for retroviral transduction of parental NK92 and successful selection of NK92CD3$^+$ cells.
Figure 8:
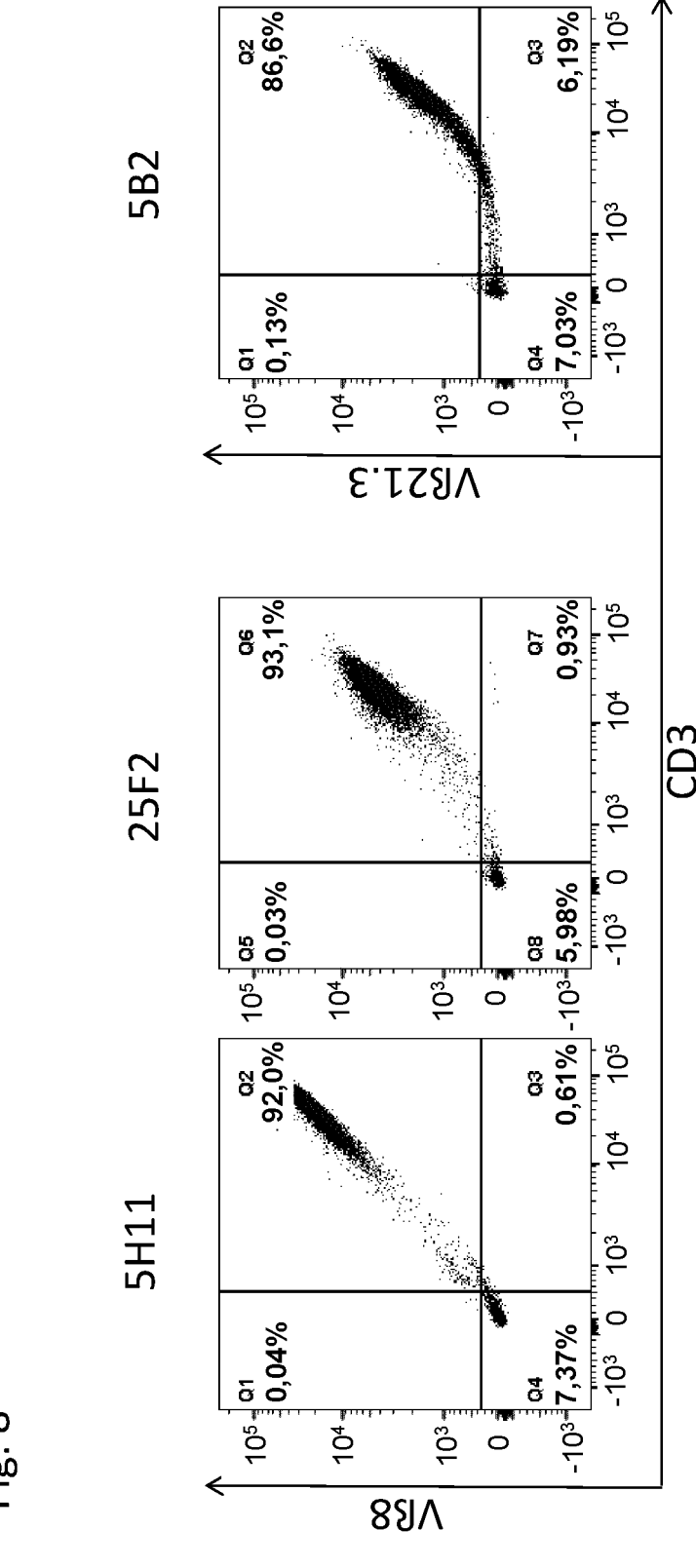
FIG. 8 shows expression of different TCRs in combination with CD3 on redirected NK92 cells. A CD3_IRES_Puromycin construct was transduced into NK92 cells, and cells were puromycin selected. Successful CD3 gene transfer was monitored upon co-transduction of three different TCRs (5H11, 25F2, 5B2). Expression of the known TCRß-chains was examined using an anti-Vß8-PE mAb reactive to 5H11 (92%), an anti-Vß8-FITC mAb reactive to 25F2 (93.1%), and an anti-Vß21.3-FITC mAb reactive to 5B2 (86.6%). CD3 was monitored using a CD3-Pacific Blue mAb. TCR/CD3 double positive cells appear in the right upper quadrant while naturally no staining is detectable for TCR and CD3 alone shown in the left upper and right lower quadrant.
Figure 9:
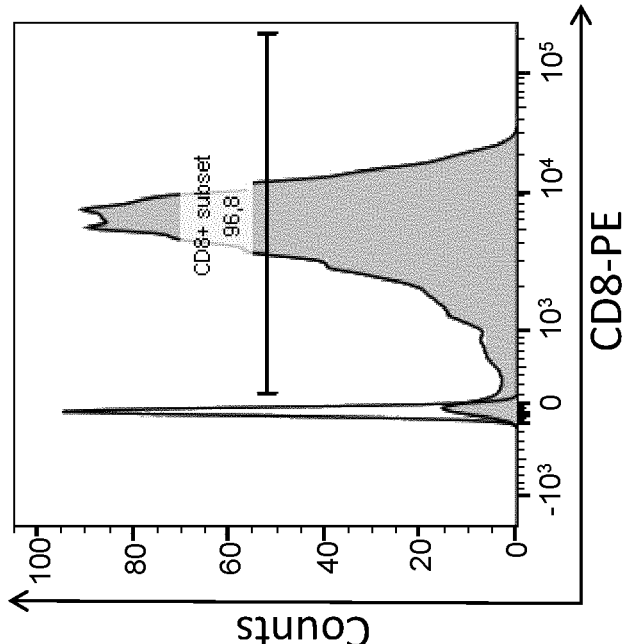
FIG. 9 illustrates that CD8 expression can be detected at the surface of NK92CD3$^+$ cells following retroviral transduction with a CD8_IRES_Neomycin construct and puromycin/neomycin selection. Cells were stained with an anti-CD8-PE mAb and a representative histogram plot shows that 96.8% of NK92CD3$^+$ cells also express CD8α1β2.
Figure 10:
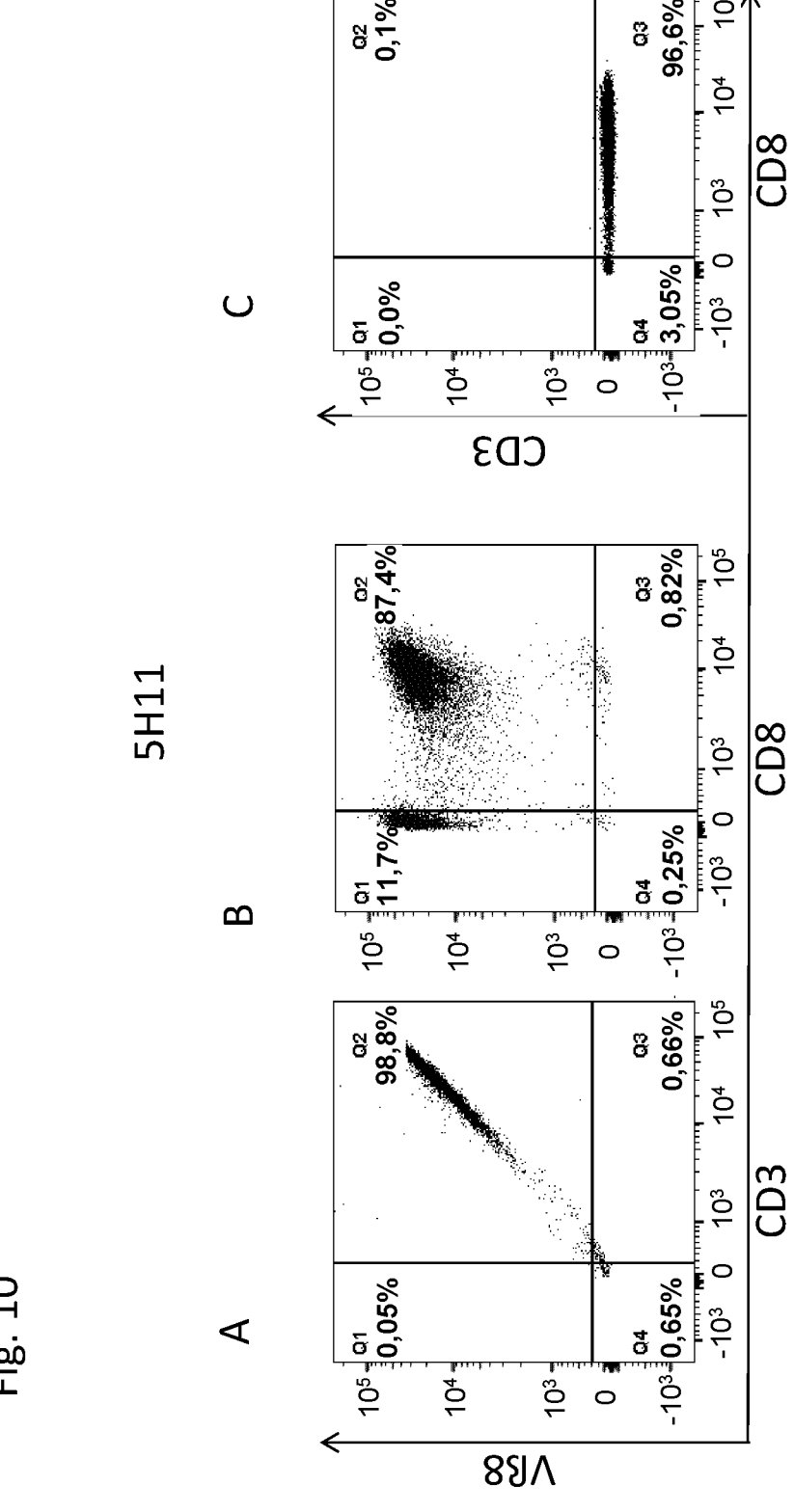
FIG. 10 demonstrates expression of the TCR 5H11 following retroviral transduction into NK92 cells previously modified to express a combination of CD3 and CD8. The TCRß-chain was detected using a Vß8-specific mAb conjugated with PE. CD3 and CD8 expression were examined with anti-CD3-APC and anti-CD8-APC mAbs, respectively. Retroviral TCR gene transfer in NK92CD3$^+$CD8$^+$ cells resulted in 98.8% TCR$^+$CD3$^+$ cells (FIG. 10A) and 87.4%

TCR$^+$CD3$^+$ cells stained for co-expression of CD8 (FIG. 10B) while virtually no (0.1%) CD3 was detectable in NK92CD3$^+$CD8$^+$ control cells due to the absence of TCR expression (FIG. 10C).

Figure 11:
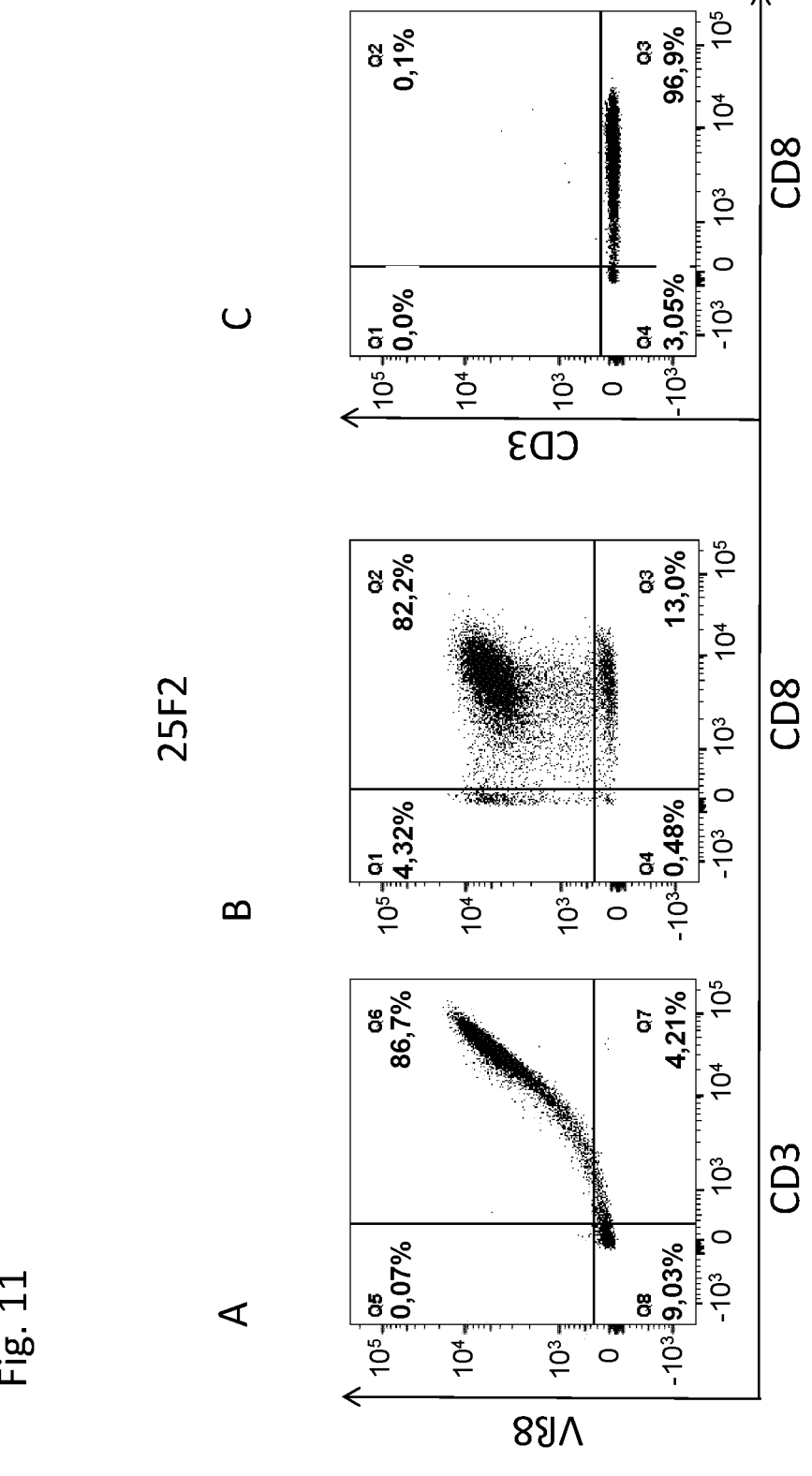

FIG. 11 shows expression of the TCR 25F2 following retroviral transduction. The TCRß-chain of TCR 25F2 was detected using a Vß8-specific mAb conjugated with FITC. CD3 and CD8 expression was analyzed with anti-CD3-Pacific Blue and anti-CD8-PE mAbs, respectively. TCR transduction resulted in 86.7% 25F2CD3$^+$ NK92 cells (FIG. 11A) and 82.2% of 25F2CD3$^+$CD8$^+$ cells (FIG. 11B) while 0.1% of TCR/CD3 expression was observed in non TCR transduced NK92CD3$^+$CD8$^+$ cells (FIG. 11C).

Figure 12:
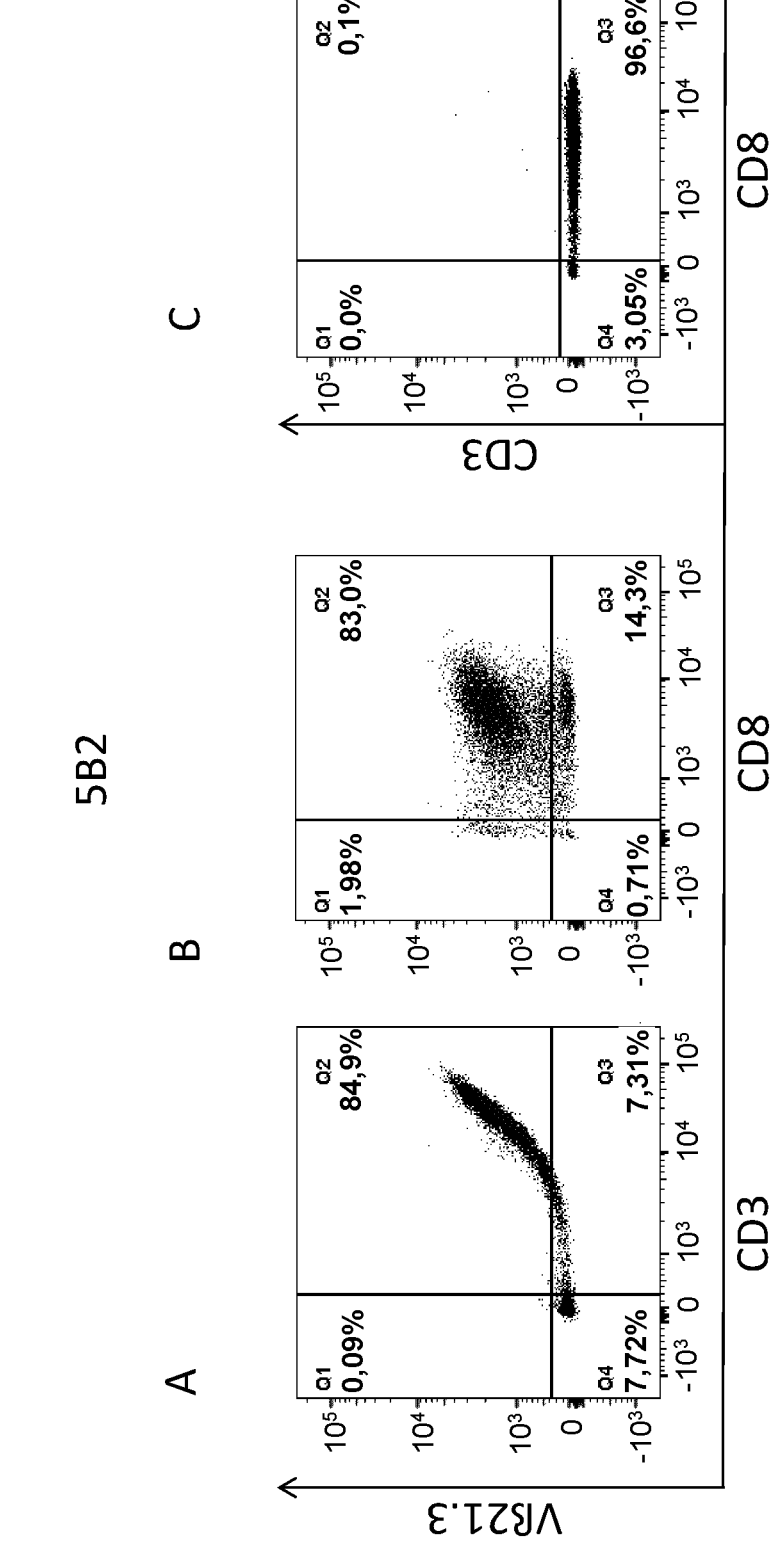

FIG. 12 demonstrates expression of the TCR 5B2 following retroviral transduction of NK92CD3$^+$CD8$^+$ cells. The TCR ß-chain of TCR 5B2 was detected using a Vß21.3-specific mAb labeled with FITC. CD3 and CD8 expression was examined by staining with anti-CD3-Pacific Blue and anti-CD8-PE mAbs, respectively. FIG. 12A illustrates the percentage of TCR 5B2 transduced NK92CD3$^+$CD8$^+$ expressing 5B2 and CD3 (84.9%) while FIG. 12B depicts the 5B2CD3$^+$CD8$^+$ NK92 cells (83.0%). In FIG. 12C 0.1% TCR/CD3 expression was observed in non TCR transduced NK92CD3$^+$CD8$^+$ cells.

Figure 13:
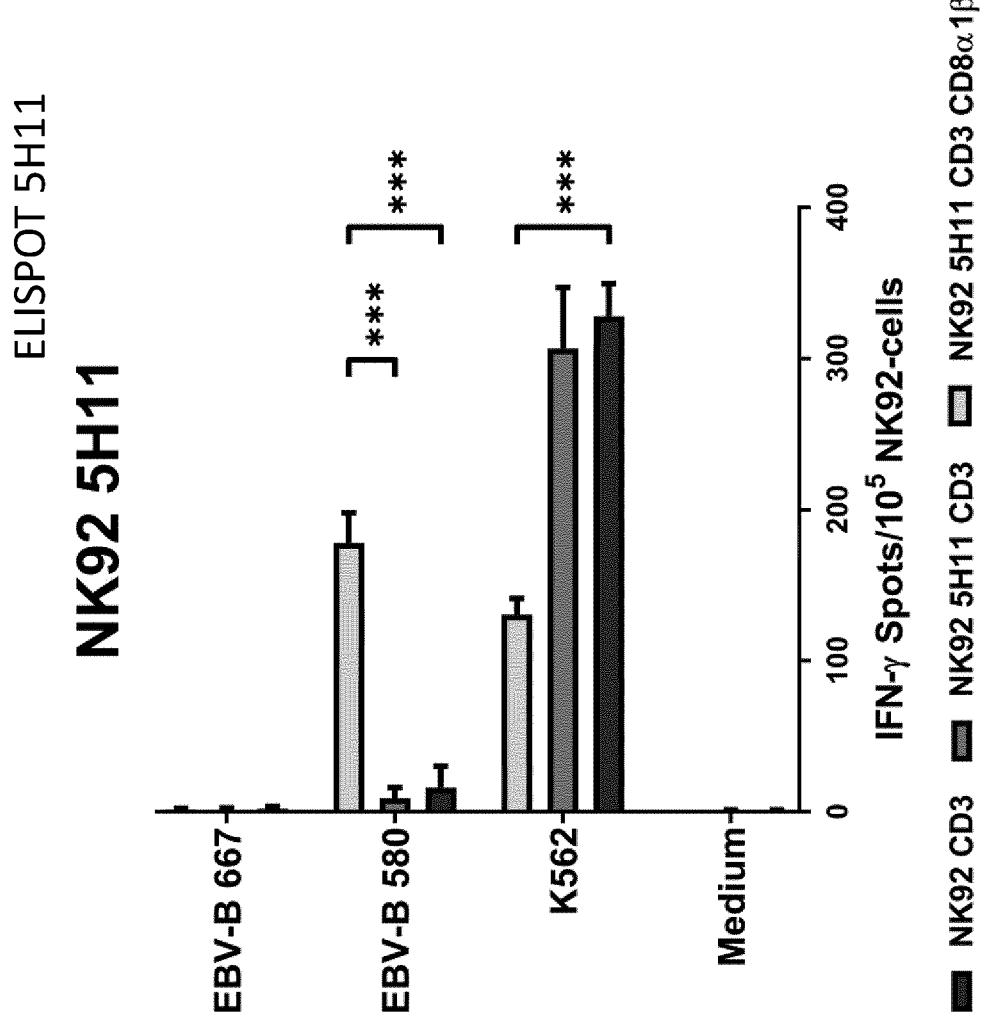

FIG. 13 depicts the results of an IFN-γ ELISPOT assay following overnight stimulation of 5H11 TCR-redirected NK92CD3$^+$CD8$^+$ cells with the HLA-matched, EBV-immortalized B cells (B-LCL) of patient MZ-580 (EBV-B580). Non-HLA-matched B-LCL (EBV-6667) were used as specificity control while K562 cells served as target control for NK cell mediated responses. Non TCR transduced NK92CD3$^+$ and 5H11CD3$^+$ NK92 were included as effector controls. Medium; effector cells without target cells (B-LCL, K562).

Figure 14:
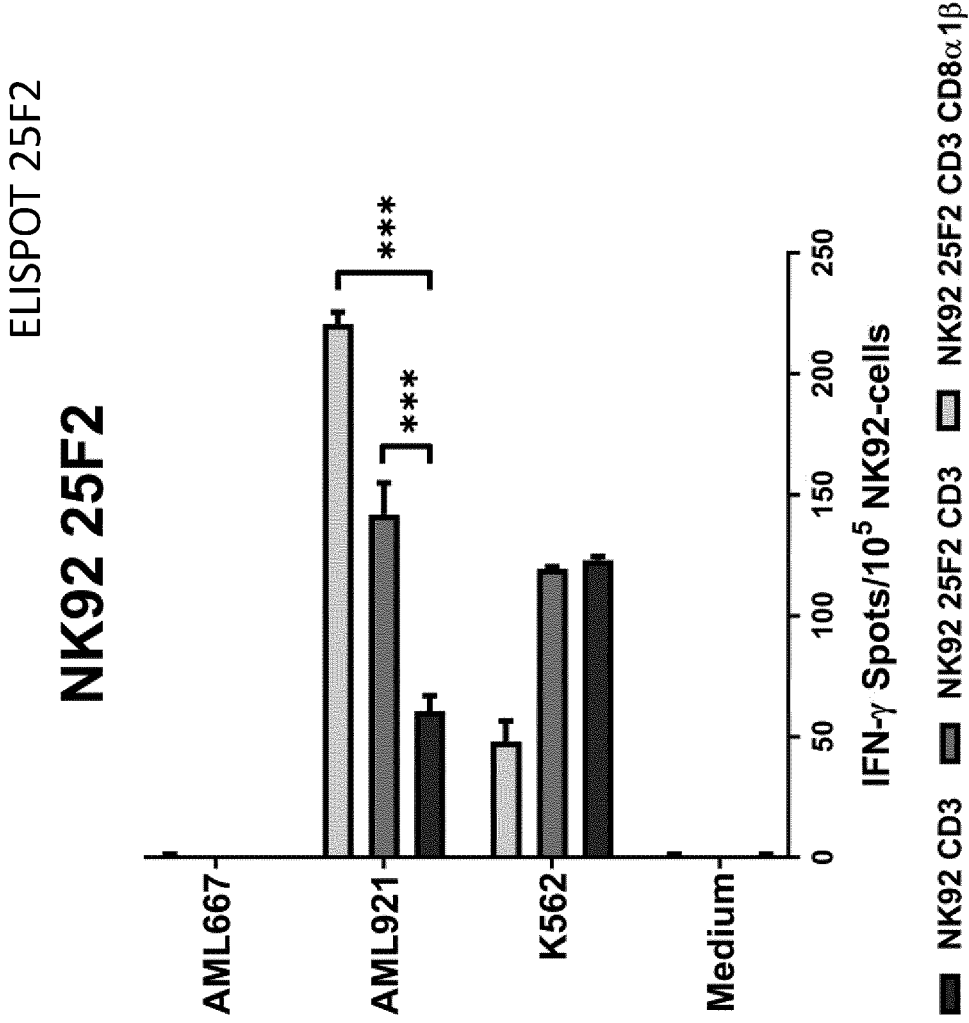

FIG. 14 shows the results of an IFN-γ ELISPOT assay following overnight stimulation of 25F2 TCR-redirected NK92CD3$^+$ and NK92CD3$^+$CD8$^+$ cells with HLA-matched AML blasts (MZ-921). AML MZ-667 and K562 cells were used as specificity controls for non HLA-matched and NK-cell mediated responses. Non TCR transduced NK92CD3$^+$ served as effector controls. Medium; effector cells without target cells (AML, K562).

Figure 15:
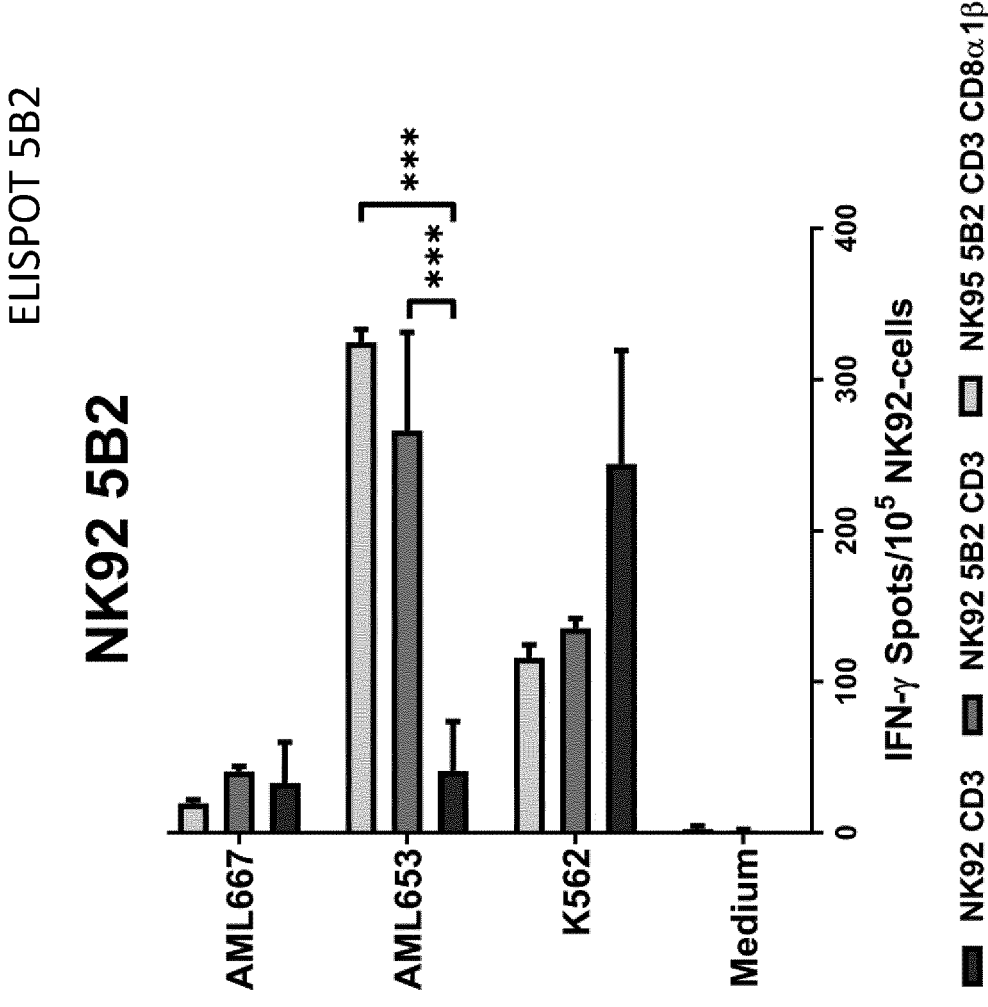

FIG. 15 illustrates the results of an IFN-γ ELISPOT assay following overnight stimulation of 562 TCR-redirected NK92CD3$^+$CD8$^+$ and NK92CD3$^+$ cells with HLA-matched AML blasts derived from patient MZ 653. AML 667 and K562 cells served as specificity controls for non-HLA matched controls and NK cell mediated responses. Non TCR transduced NK92CD3$^+$ served as effector controls. Medium; effector cells without target cells (AML, K562).

Figure 16:
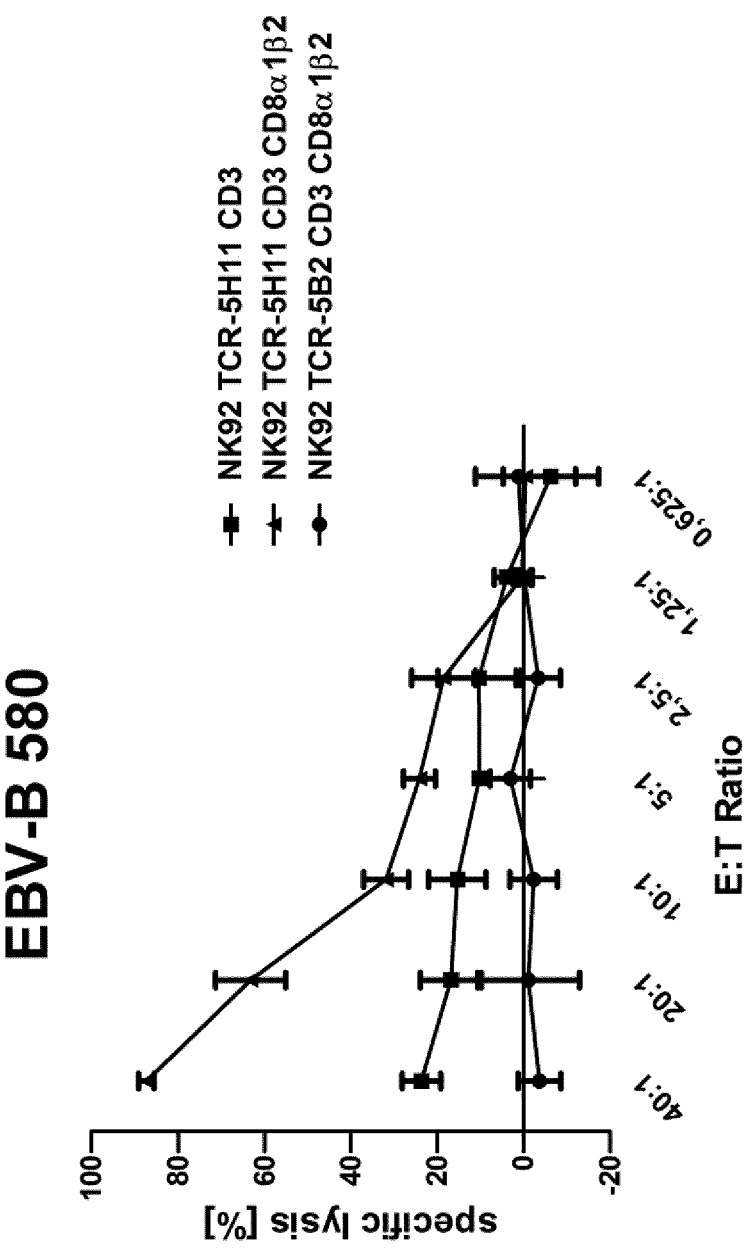

FIG. 16 depicts TCR 5H11 mediated killing of 5H11CD3$^+$CD8$^+$ NK92 cells measured by reduction of a luciferin/ATP-dependent bioluminescence signal (BLI) of B-LCL target cells constitutively expressing a firefly luciferase reporter gene (FLuc). TCR 5H11-redirected NK92CD3$^+$ and 5H11CD3$^+$CD8$^+$ NK92 as well as TCR 562-expressing NK92CD3$^+$CD8$^+$ and non TCR transduced NK92CD3$^+$ were cocultured in triplicates at indicated ratios with FLuc expressing HLA-matched, EBV immortalized B cells (B-LCL) from patient MZ 580 in the presence of D-Luciferin. After 18 h of coculture remaining BLI was determined with a BMG Fluostar Omega Reader at 10 s integration time per well and TCR-specific lysis was quantified by deterioration of FLuc-signal compared to residual luminescence of target cells cocultured with non TCR transduced NK92CD3$^+$. TCR 5B2-redirected NK-92CD3$^+$CD8$^+$ served as specificity control.

Figure 17:
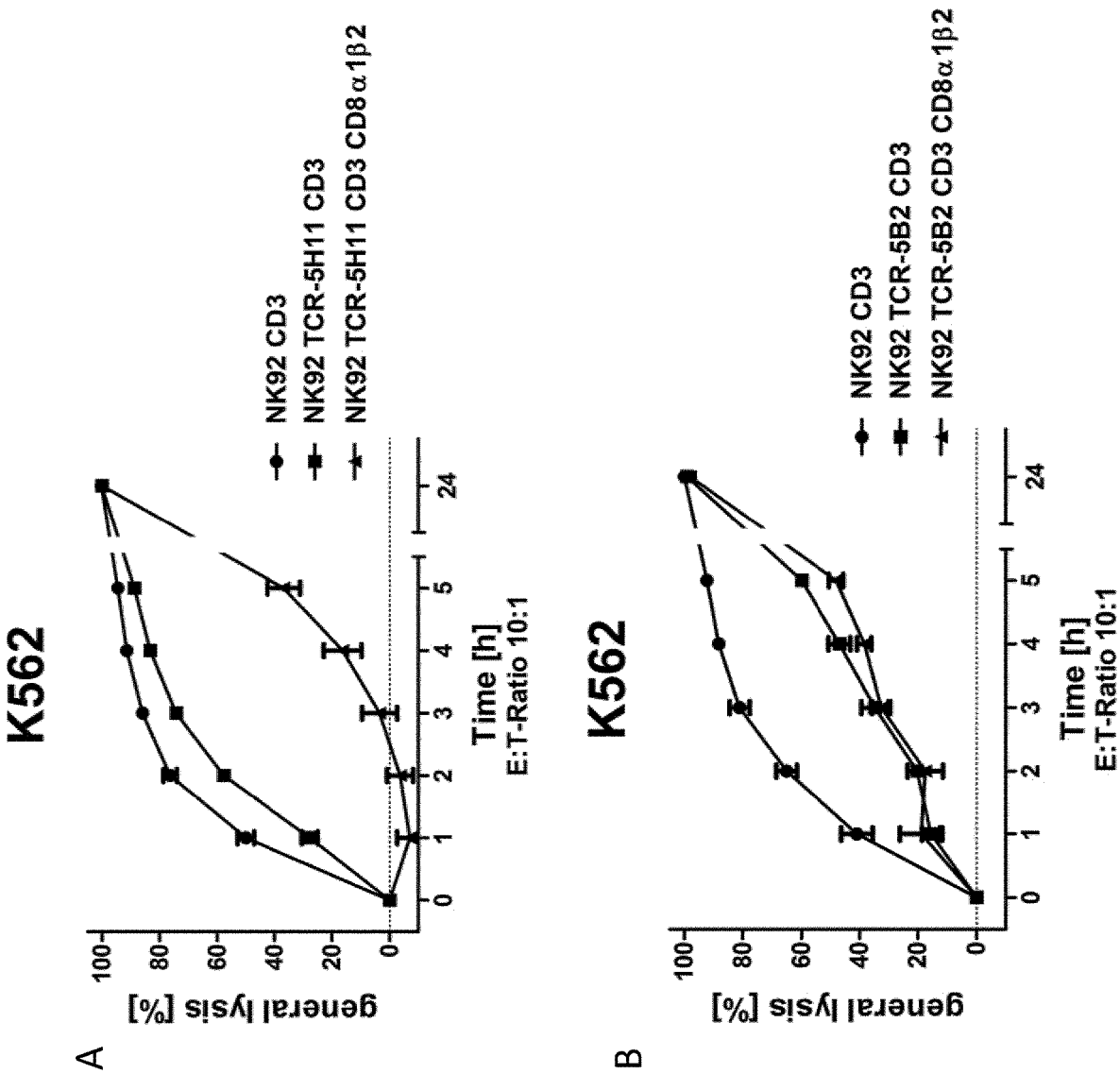

FIG. 17 demonstrates NK-cell mediated cytotoxicity of the TCR 5H11 and 5B2 transduced NK92 subsets measured by reduction of luciferin/ATP-dependent BLI in FLuc-K562 target cell transfectants. FLuc-expressing K562 were co-cultured with non TCR transduced NK92CD3$^+$ as well as with TCR 5H11 or 5B2 expressing NK92CD3$^+$ and NK92CD3$^+$CD8$^+$ at an effector to target ratio of 10:1 in triplicates in the presence of D-Luciferin. Remaining BLI was examined every hour over a 5 h time period and after 24 h of co-culture with BMG Fluostar Omega Reader at 10 s integration time per well. General lysis was quantified as deterioration of FLuc-signal compared to luminescence of target cells cultivated with no effectors.

Figure 18:
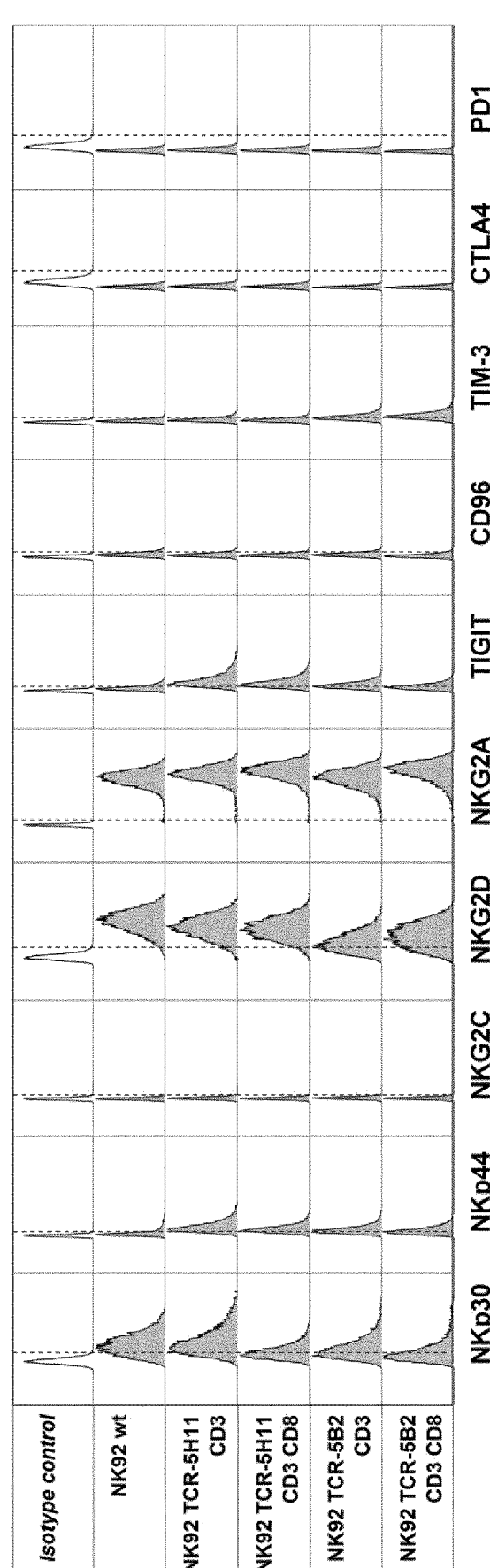

FIG. 18 shows expression profiling of different activating and inhibiting markers monitored on wild type (wt) NK92, NK92CD3$^+$ and NK92CD3$^+$CD8$^+$ cells. Modified NK cells have been retrovirally transduced to express the TCR 5H11 and 5B2. The following mAb-conjugates were used to detect expression by flow cytometry: anti-NKp30-APC, anti-NKp44-PE, anti-NKG2C-PE, anti-NKG2D-APC, anti-NKG2A-PE, anti-TIGIT-PE, anti-CD96-PE, anti-TIM3-PE, anti-CTLA4-APC, anti-PD1-APC. While NKp30 expression appears to be clearly reduced in NK92-5B2CD3$^+$, NK92-5B2CD3$^+$CD8$^+$ and NK92-5H11CD3$^+$CD8$^+$ cells, no further significant changes in the expression level of other markers could be detected between the NK92 cell populations.

MATERIAL AND METHODS

Donors and Patients

Healthy donors of T lymphocytes and leukaemia patients participated in the study after informed consent in accordance with the Helsinki protocol. High-resolution genomic HLA typing was performed according to standard procedures.

Primary Cells and Cell Lines

NK92 cells were cultured in Alpha-MEM medium supplemented with 20% fetal calf serum (FCS) (PAA Laboratories, Pasching/Austria), 1% Penicillin/Streptomycin (Gibco/Thermofisher Scientific), 0.2M Inositol (Applichem, Darmstadt, Germany), 0.02M Folic acid (Applichem), 0.1 mM Mercaptoethanol (Sigma Aldrich, Steinheim, Germany), and 200 IU recombinant human (rh) IL-2/ml (Novartis). Medium was exchanged every 2-3 days. AML blasts (AML 667, 921 and 653) were isolated either from peripheral blood, bone marrow biopsies, or therapeutic leukapheresis products of patients by standard Ficoll separation and cryopreserved until use. All leukaemia samples contained >95% leukaemia blasts. EBV-transformed B-lymphoblastoid cell lines (B-LCL) were generated from patient peripheral blood mononuclear cells (PBMC) according to standard procedures. The chronic myelogenous leukaemia (CML) cell line K562 was cultured using standard protocols.

Generation of AML-Reactive CD8 CTL-Clones 5H11, 25F2 and 5B2

Naive CD8$^+$CD45RA$^+$ T cells of healthy donors were MACS® isolated (Naive CD8$^+$ T cell Isolation Kit, Miltenyi Biotec, Bergisch Gladbach, Germany) to be stimulated at 1:1 ratio with fully HLA-matched AML blasts (5×10$^4$ cells/well) and autologous feeder cells (CD45RA$^-$ PBMC) (5×10$^4$ cells/well) to generate CTL clones. AML blasts and feeder cells were irradiated prior to co-cultures (35 Gy for feeder cells, 60 Gy for AML blasts). Medium was AIM-V (Gibco/Life Technologies, Thermofisher Scientific) supplemented with 10% pooled and heat inactivated human serum and experimentally determined optimal concentrations of 5 ng/mL of each rhIL-7 and rhIL-15 (Peprotech), 1 ng/mL rhIL-12 (R&D Systems), and 10 ng/mL rhIL-21 (Biomol). T-cell cultures were expanded by weekly addition of irradiated AML blasts and cytokines. From d14 onward, IL-12 was replaced by 100 IU/mL rhIL-2 (Novartis). T cells were regularly tested for reactivity using IFN-γ ELISPOT assays. Clonality of T cells was determined by flow cytometry using Vß-profiling monoclonal antibodies (mAbs) (Beckman Coulter).

Cloning of TCR Genes

Cloning of TCR genes was performed as originally described by Birkholz K et al. (A fast and robust method to clone and functionally validate T-cell receptor, Journal of Immunol. Methods. 2009 (346): 45-54). Briefly, total RNA of a T-cell clone was isolated using the RNeasy Mini Kit (Qiagen, Hilden, Germany) according to the manufacturers' instructions. Synthesis and amplification of cDNA was performed as originally described for tumour cell RNA (Harris et al., 2005). In brief, reverse transcription was performed on ≤1.0 μg of RNA. Ten pmol of the 64T-primer (CGATAAAAGCTCCGGGGATAACAGAT63VN, V=A,G, C; N=A,C,G,T) and 10 pmol of the capswitch oligo (AAGCAGTGGTAACAACGCAGAGT ACGCGGG) were added to the RNA, and primer annealing was performed for 2 min at 72° C., followed by 1 min at 4° C. The cDNA synthesis was performed using Supercript II reverse transcriptase (Invitrogen/Thermofisher Scientific), first strand buffer (Invitrogen), 100 mM DTT (Invitrogen), 10 mM dNTPs (Invitrogen) and subsequent incubation for 60 min. at 42° C., followed by 1 min. at 4° C. Amplification of the cDNA was performed by adding Advantage 2 polymerase (Clonetech) in the presence of 64T-primer and T7-Capswitch-primer (TTATACGACTCACTATAGG GAGGAAGCAGTGGTAACAACG CAGAGT) and dNTPs using 20 PCR reaction cycles. The quality of the amplified cDNA was analyzed by standard gel electrophoresis. Next, the complete cDNA of the TCRα- and β-chains were amplified using primers designed according to the sequence results. The amplified TCR chains were then cloned for further use and sequenced. All different regions of the TCRs were determined using the IMGT V-QUEST database (IMG/V-QUEST; www.imgt.orq).

Cloning of CD8 and CD3 Coreceptors

According to Szymczak, A. L., et al. (2004) ("Correction of multi-gene deficiency in vivo using a single 'self-cleaving' 2A peptide-based retroviral vector." Nature Biotechnology 22: 589.) a polycistronic vector encoding the δ-, ε-, γ-, ζ-subunit of the human CD3 complex was cloned for retroviral transduction. In order to generate retroviral CD8-expression vectors, RNA was isolated from the original CTL clones, the TCRs 5B2 and 25F2 derived from, using the RNeasy Mini Kit (Qiagen, Hilden, Germany). Upon reverse transcription with SuperScript III reverse transcription kit (ThermoFisher Scientific, Waltham, USA) the CD8α- and β-chains expressed by the original CTL were amplified via PCR and In-Fusion cloning into pMX retroviral vector backbone was performed using NEBuilder HIFI DNA-Assembly Kit (New England Biolabs GmbH, Frankfurt, Germany).

Generation of Retroviral Particles for Transduction of NK92 Cells

For the generation of retrovirus, a second-generation retrovirus producer cell line (Phoenix-Ampho) was utilized that stably expresses gag-pol and the envelope vector pColtGalv. The day before transfection, 2.5×10$^6$ Phoenix cells were plated in a 100 mm cell culture dish. For transfection, 5 μg of each vector for packaging and virus envelope (pHit60 and pColtGALV) and 10 μg of the retroviral transfer vector were mixed in Opti-MEM medium with polyethylen-eimine-(PEI) and allowed to form PEI:DNA complexes. Then, the mixture was filled up to a total volume of 5 mL with Opti-MEM and applied dropwise onto Phoenix cells prewashed with PBS. After 4 h of incubation, the mixture was replaced by 5 mL fresh medium (complete Alpha-MEM medium as described above) and the cells were cultivated for 48 h. Retroviral supernatant was harvested 48 hours after transfection and sterile filtered using a 0.45 μm pore sized filter.

Retroviral Transduction of NK92 Cells

For the transduction of NK92 cells the spin infection method using polybrene was applied. Polybrene acts as a polycationic linker molecule to increase infection efficiency. One×$10^6$ NK92 cells/well were resuspended in 1 ml freshly harvested retroviral particles supernatant and plated into a 24-well plate. After the addition of 5 μg mL$^{-1}$ polybrene, the plate was centrifuged at 2,000 rpm for 90 min at 32° C. without deceleration. Thereafter, the cells were incubated for 24 h at 37° C. in the retroviral particles supernatant. Afterwards cells were harvested, counted and washed in order to remove residual retroviral particles. Cells were then resuspended in complete NK92 cell medium including rhIL-2 as described. For selection of successfully transduced NK92 cells neomycin or puromycin was added at a final concentration of 500 μg/mL (G418) and 1 μg/ml (Puromycin) for up to 7 days. Since transduction of CD8 conferred neomycin resistance while NK92CD3$^+$CD8$^+$ cells were also resistant to puromycin, additional expression of a given TCR was achieved by 2-3 rounds of enrichment of TCRCD3$^+$CD8$^+$ NK92 cells using anti human CD3 mAb-conjugated immunomagnetic beads and magnetic cell sorting (MACS®, Miltenyi Biotec) or fluorescence activated cell sorting (FACS®) on a BD Aria FACS-sorter. Expression of CD3, CD8 and TCRs was regularly monitored by flow cytometry as described. For continuous cultivation, the cells were seeded at 2 to 3×$10^5$ cells/ml in a small culture flask.

Flow Cytometric Analysis

NK92 cells were incubated with FITC-, PE-, APC- or Pacific Blue-conjugated monoclonal antibodies (mAbs) specific for the indicated antigens TCR-Vβ8 (Biolegend), TCR-Vβ21.3 (Beckman Coulter), CD3, CD8, CTLA4, PD1 (all from BD Biosciences) CD96 (Santa Cruz Biotechnol.), NKG2A, NKG2C (both from Miltenyi Biotec), TIGIT, NKG2D, NKp30, NKp44 and TIM-3 (all from Biolegend) for 15 min at 22° C. and washed afterwards. $10^4$-$10^5$ events of viable cells were analyzed on a BD FACSCanto II flow cytometer. eGFP expressing B-LCL transfectants were measured by GFP expression using the FITC channel.

IFN-γ Enzyme-Linked Immunosorbent Spot (ELISpot) Assay

Multiscreen HTS™ IP plates (Millipore, Bedford, MA) were coated with 10 μg/mL mAb anti-hIFN-γ 1-DIK (Mabtech, Stockholm, Sweden). Parental or genetically modified NK 92 cells were seeded at 1×$10^5$/well and target cells at 1×$10^5$/well in Alpha-MEM medium supplemented as described above. Modified NK92 and targets seeded alone served as background controls. After overnight incubation at 37° C., plates were washed with PBS including Tween 20 and captured IFN-γ was detected by biotinylated mAb anti-hIFN-γ 7-B6-1 (Mabtech) at 2 μg/mL, a avidin/horseradish peroxidase complex and AEC solution to visualize captured IFN-γ. Spots were developed and counted using a computer-assisted video image analysis system (KS ELISpot 4.9; Zeiss, Jena, Germany). Shown results are means±SD of representative duplicates.

Evaluation of TCR-Mediated Cytotoxicity In Vitro

To measure the effect of TCR redirection and CD8 co-expression on NK92 cytotoxicity, 1×$10^4$ FLuc transduced K562, EBV-B-LCL 580 and 667 target cells were cocultured per well in triplicates with NK92 effectors at E:Ts from 40:1 to 0.625:1 in black 96-well plates in the presence of the FLuc-substrate D-Luciferin (Thermo Scientific). After 18 h of incubation relative luminescence units were determined by the FluostarOmega-Reader (BMG LABTECH, Offenburg, Germany) with 10 s integration time per well. Specific lysis of CD8 and or TCR positive cells was quantified by loss of FLuc signal and normalized to untransduced NK92 according to the following equation: specific lysis [%]= (killing by NK92 CD3—killing by TCR$^+$ NK92)/killing by NK92 CD3×100. General lysis was determined as follows: general lysis [%]=100*(RLU of targets without effector cells–RLU of targets cocultured with TCR$^+$ NK92)/(RLU of targets without effector cells RLU of maximal lysis control).

Statistics

Statistical data analysis was conducted with Graph Pad Prism Software using two-way ANOVA or multiple t-test using the Bonferroni-Dunn method. P<0.05 was considered statistically significant. Mean values and standard deviations (SD) were calculated from at least 2 independent experiments.

---

The invention claimed is:

1. A modified natural killer 92 (NK-92) cell co-expressing:

(1) an antigen-specific functional T cell receptor (TCR) comprising an alpha chain and a beta chain, (2) CD3, said CD3 consisting of a CD3 γ chain, a δ chain, two ε chains, and two ζ chains, and (3) CD8 and/or CD4.

2. The modified NK-92 cell according to claim 1, wherein the TCR originates from 5B2, 25F2 or 5H11 cells.

3. The modified NK-92 cell according to claim 2, wherein the 5B2 TCR is composed of an alpha chain encoded by SEQ ID NO: 1 and a beta chain encoded by SEQ ID NO: 2.

4. The modified NK-92 cell according to claim 2, wherein the 25F2 TCR is composed of an alpha chain encoded by SEQ ID NO: 3 and a beta chain encoded by SEQ ID NO: 4.

5. The modified NK-92 cell according to claim 2, wherein the 5H11 TCR is composed of an alpha chain encoded by SEQ ID NO: 5 and a beta chain encoded by SEQ ID NO: 6.

6. The modified NK-92 cell according to claim 1, wherein the TCR is a fusion protein with CD3 and CD8 or CD4 expressed by the NK-92 cell.

7. A modified natural killer 92 (NK-92) cell according to claim 1 for use as a medicament.

8. A modified natural killer 92 (NK-92) cell according to claim 1 for use in cancer therapy.

9. The modified NK-92 cell according to claim 8, wherein the cancer is a solid tumour.

10. A modified natural killer 92 (NK-92) cell according to claim 1 for use in the prevention or treatment of leukaemia and related disorders.

11. The modified NK-92 cell according to claim 10, wherein the leukaemia is selected from acute myeloid leukaemia (AML), chronic lymphocytic leukemia (CLL), acute lymphocytic leukaemia (ALL), chronic myeloid leukaemia (CML), chronic myelomonocytic leukaemia (CMML), eosinophilic leukaemia, hairy cell leukaemia, Hodgkin's lymphoma (HL), multiple myeloma (MM), non-Hodgkin's lymphoma (NHL), myeloproliferative disorders or myelodysplastic syndrome (MDS).

12. A pharmaceutical composition, comprising a modified natural killer 92 (NK-92) cell according to claim 1, and at least one pharmaceutically acceptable carrier or excipient.

13. The modified NK-92 cell according to claim 9, wherein the solid tumour is a sarcoma, a carcinoma, a melanoma, or a lymphoma.

\* \* \* \* \*